(12) United States Patent
Hu et al.

(10) Patent No.: US 12,730,110 B2
(45) Date of Patent: Sep. 8, 2026

(54) DEVICES AND METHODS FOR DETECTING A TARGET ANALYTE OF INTEREST

(71) Applicant: DrinkSavvy, Inc., Brooklyn, NY (US)

(72) Inventors: Min Hu, Brooklyn, NY (US); Jacob Trevino, New York, NY (US); Brendan Walker, Atlantic Highlands, NJ (US); Lilian Lamech, New York, NY (US)

(73) Assignee: Chemeleon Inc., Brooklyn, NY (US)

( * ) Notice: Subject to any disclaimer, the term of this patent is extended or adjusted under 35 U.S.C. 154(b) by 750 days.

(21) Appl. No.: 18/040,633

(22) PCT Filed: Aug. 3, 2021

(86) PCT No.: PCT/US2021/044403
§ 371 (c)(1),
(2) Date: Feb. 3, 2023

(87) PCT Pub. No.: WO2022/031748
PCT Pub. Date: Feb. 10, 2022

(65) Prior Publication Data

US 2023/0296614 A1 Sep. 21, 2023

Related U.S. Application Data

(60) Provisional application No. 63/060,597, filed on Aug. 3, 2020.

(51) Int. Cl.
*G01N 33/68* (2006.01)
*G01N 21/78* (2006.01)
(Continued)

(52) U.S. Cl.
CPC ............ *G01N 33/68* (2013.01); *G01N 21/78* (2013.01); *G01N 33/5308* (2013.01); *G01N 33/54373* (2013.01); *G01N 2333/79* (2013.01)

(58) Field of Classification Search
CPC .. G01N 21/554; G01N 21/78; G01N 2333/79; G01N 33/52; G01N 33/5308;
(Continued)

(56) References Cited

U.S. PATENT DOCUMENTS 5,478,751 A 12/1995 Oosta et al.
8,339,597 B2 12/2012 Dal Negro et al.
(Continued)

FOREIGN PATENT DOCUMENTS

AT 508710 B1 6/2011
CN 1922486 A 2/2007
(Continued)

OTHER PUBLICATIONS

Australian Examination Report No. 1 for Australian Patent Application No. 2017374052, dated Nov. 5, 2021 (3 pages).
(Continued)

*Primary Examiner* — Jennifer Wecker
(74) *Attorney, Agent, or Firm* — Michael T. Abramson; Jordan IP Law, LLC

(57) ABSTRACT

A sensor for detecting an analyte of interest in a fluid sample includes (i) a structure having a plurality of surficial walls that define a plurality of air gaps in the structure and (ii) a binding material. The structure is configured such that both a fluid sample lacking the analyte of interest and a fluid sample containing the analyte of interest are able to penetrate the plurality of air gaps. The binding material, which is present on the plurality of surficial walls, is able to bind the analyte of interest. The sensor is configured such that, when the analyte of interest binds to the binding material, a change in surface energy results within the plurality of surficial walls.

19 Claims, 25 Drawing Sheets

(51) Int. Cl.
*G01N 33/53* (2006.01)
*G01N 33/543* (2006.01)

(58) Field of Classification Search
CPC . G01N 33/542; G01N 33/54373; G01N 33/68
See application file for complete search history.

(56) References Cited

U.S. PATENT DOCUMENTS 8,673,237 B2 3/2014 Schalkhammer
9,285,352 B2 3/2016 Abramson et al.
9,464,985 B2 10/2016 Liu et al.
9,676,621 B2 6/2017 Chen et al.
11,415,522 B2 8/2022 Hu
11,815,464 B2 11/2023 Hu
2006/0034729 A1 2/2006 Poponin
2007/0155021 A1* 7/2007 Zhang .............. G01N 33/54346 977/902
2009/0009756 A1* 1/2009 Yamamichi ............ G01N 21/66 356/246
2009/0026290 A1 1/2009 Fox
2009/0273779 A1* 11/2009 Baumberg ........... G01N 21/658 204/192.12
2009/0298712 A1 12/2009 Kiryukhin et al.
2009/0302235 A1 12/2009 Himmelhaus
2010/0046902 A1 2/2010 Kaplan et al.
2011/0050431 A1 3/2011 Hood et al.
2011/0198222 A1 8/2011 Bhatia et al.
2011/0205543 A1 8/2011 Offermans et al.
2012/0160725 A1 6/2012 Abramson
2012/0236298 A1* 9/2012 Stuke ................... G01N 21/658 356/301
2012/0293802 A1 11/2012 Ozin et al.
2012/0309047 A1 12/2012 Kofinas et al.
2013/0157254 A1* 6/2013 Sengupta ......... G01N 33/54373 435/7.1
2014/0106468 A1 4/2014 Boersma
2014/0334005 A1 11/2014 Omenetto et al.
2015/0104861 A1 4/2015 Abramson et al.
2016/0025635 A1 1/2016 Li et al.
2016/0140994 A1 5/2016 Chen et al.
2016/0178600 A1 6/2016 Ahira et al.
2016/0282275 A1 9/2016 Aizenberg et al.
2017/0160205 A1 6/2017 Lee et al.
2018/0003706 A1 1/2018 Trenholm et al.
2019/0265169 A1 8/2019 Hu
2019/0339266 A1* 11/2019 Liu ....................... G06T 7/0014

FOREIGN PATENT DOCUMENTS

CN 102012421 A 4/2011
CN 103849674 A 6/2014
CN 104428651 A 3/2015
CN 106662539 A 5/2017
EP 2500314 A1 9/2012
EP 2761269 B1 8/2014
GB 2411958 A 9/2005
GB 2418248 A 3/2006
JP 2006317442 A 11/2006
JP 2009535604 A 10/2009
KR 101255752 B1 4/2013
WO 2008045596 A2 4/2008
WO 2010088585 A1 8/2010
WO 2011017726 A1 2/2011
WO 2011109473 A1 9/2011
WO 2011136548 A2 11/2011
WO 2012054121 A2 4/2012
WO 2012078351 A2 6/2012
WO 2012087342 A1 6/2012
WO 2013106588 A1 7/2013
WO 2013154770 A1 10/2013
WO 2013170377 A1 11/2013
WO 2015157691 A1 10/2015
WO 2016012682 A1 1/2016
WO 2016025430 A1 2/2016
WO WO-2018107038 A1 * 6/2018 ........... G01N 21/554
WO WO-2018231962 A1 * 12/2018 ............ G01N 21/78
WO 2021262163 A1 12/2021

OTHER PUBLICATIONS

Australian Notice of Acceptance for Australian Patent Application No. 2017374052, dated Oct. 18, 2022 (3 pages).
European Examination Report for European Patent Application No. 17826019.6, dated Nov. 16, 2021 (7 pages).
International Search Report and Written Opinion for International Application No. PCT/US2017/065333, mailed May 23, 2018 (15 pages).
Non-Final Office Action for U.S. Appl. No. 16/427,039 dated Apr. 12, 2021, 15 pages.
Notice of Allowance for U.S. Appl. No. 16/427,039 dated Nov. 10, 2021, 8 pages.
Corrected Notice of Allowability for U.S. Appl. No. 16/427,039 dated Jan. 27, 2022, 4 pages.
Non-Final Office Action for U.S. Appl. No. 17/671,383 dated Dec. 8, 2023, 8 pages.
Notice of Allowance for U.S. Appl. No. 17/671,383 dated May 8, 2024, 9 pages.
Corrected Notice of Allowability for U.S. Appl. No. 17/671,383 dated Aug. 5, 2024, 35 pages.
Corrected Notice of Allowability for U.S. Appl. No. 17/671,383 dated Sep. 12, 2024, 42 pages.
Corrected Notice of Allowability for U.S. Appl. No. 17/671,383 dated Sep. 25, 2024, 42 pages.
Non-Final Office Action for U.S. Appl. No. 18/801,603 dated Feb. 18, 2026, 27 pages.
Office Action mailed Aug. 10, 2023 in Canadian Application No. 3067221, 5 pages.
Office Action mailed May 22, 2024 in Canadian Application No. 3067221, 3 pages.
Allowance mailed Aug. 22, 2025 in Canadian Application No. 3067221, 1 page.
Office Action and English translation for Chinese Application No. 201880052536.4 mailed Jun. 30, 2022, 16 pages.
International Search Report and Written Opinion for International Application No. PCT/US2018/037304, dated Sep. 28, 2018, 11 pages.
Notice of Allowance for U.S. Appl. No. 16/711,843 dated Mar. 17, 2023, 13 pages.
Corrected Notice of Allowability for U.S. Appl. No. 16/711,843 dated Jun. 8, 2023, 6 pages.
Notice of Allowance for U.S. Appl. No. 18/336,199 dated Oct. 25, 2024, 10 pages.
International Search Report and Written Opinion for International Application No. PCT/US2021/044403, dated Nov. 15, 2021, 11 pages.
Non-Final Office Action for U.S. Appl. No. 18/455,812 dated Mar. 25, 2026, 14 pages.
Billard A, Laval V, Fillinger S, Leroux P, Lachaise H, Beffa R, Debieu D. The allele-specific probe and primer amplification assay, a new real-time PCR method for fine quantification of single-nucleotide polymorphisms in pooled DNA. Appl Environ Microbial. Feb. 2012;78(4):1063-8. (Year: 2012).
Burgess, et al., "Encoding Complex Wettability Patterns in Chemically Functionalized 3D Photonic Crystals", Journal of the American Chemical Society, Jully 18, 2011, 3 pages.
Burgess, et al., "Wetting in Color: Colorimetric Differentiation of Organic Liquids with High Selectivity", ACS Nano, Dec. 20, 2011, 11 pages.
Burgess, I.B. et al. "Structural colour in colourimetric sensors and indicators," J. Mater. Chem. C, 2013, 1, 6075-6086 (12 pgs) (Year: 2013).
Dechtrirat, Decha et al., "Hybrid Material for Protein Sensing Based on Electrosynthesized MIP on a Mannose Terminated Self-Assembled Monolayer", Advanced Functional Materials, vol. 24, No. 15, Apr. 1, 2014 (pp. 2233-2239).

(56) References Cited

OTHER PUBLICATIONS

Duke et al., "Colorimetric and fluorescent anion sensors: an overview of recent developments in the use of 1,8-naphthalimide-based chemosensors", Chemical Society Reviews, 2010, 19 pages.
Geissler et al., Polymer Micropillar Arrays for Colorimetric DNA Detection, 2020, Anal. Chem. 2020, 92, 11, 7738-7745 (Year: 2020).
Hatton, et al, "Assembly of large-area, highly ordered, crack-free inverse opal films," PNAS, vol. 107, No. 23, 9 pages.
Hoopes, C.R et al. "Donor-Acceptor Pyridinium Salts for Photo-Induced Electron-Transfer-Driven Modification of Tryptophan in Peptides, Proteins, and Proteomes Using Visible Light," J. Am. Chem. Soc. 2022, 144, 6227-6236 (Year: 2022).
Hu, Jonathan et al., "Effects of nanodots on surface plasmons and electric field enhancement in nano-pillar antenna array", Conference on Lasers and Electro-optics (CLEO) and Quantum Electronics and Laser Science Conference (QELS), May 16, 2010, 2 pages.
James, Timothy D et al., "The Plasmonic Pixel: Large Area, Wide Gamut Color Reproduction Using Aluminum Nanostructures", Nano Letters 2016, 16, pp. 3817-3823.
Jiang, J. et al. "Colorimetric naked-eye recognizable anion sensors synthesized via RAFT polymerization," Journal of Polymer Science Part A: Polymer Chemistry 48(7) (2010) 1551-1556 (Year: 2010).
Kang et al, "Broad-wavelengh-range chemically tunable block-copolymer photonic gels," Nature Publishing Group, vol. 6, No. 12, Oct. 21, 2007, 4 pages.
Koster et al., Fibers Coated with Molecularly Imprinted Polymers for Solid-Phase Microextraction, 2001, Analytical chemistry, vol. 73, issue 13 (Year: 2001).
Li, Wen-Di et al., "Three-dimensional cavity nanoantenna coupled plasmonic nanadots for ultrahigh and uniform surface-enhanced Raman scattering over large area", Optics Express, Feb. 28, 2011, vol. 19, No. 5, pp. 3925-3936.
Meng, et al., "Fast screening of ketamine in biological samples based on moleculary imprinted photonic hydrogles", Analytica Chimica Acta, vol. 771, dated Feb. 8, 2013, 9 pages.
Miyata, Masashi et al., "Full-Color Subwavelength Printing with Gap-Plasmonic Optical Antennas", Nano Letters 2016, 16, pp. 3166-3172.
Nadja Popovich, "DrinkSavvy: how your straw could help you stay safe", The Guardian, Aug. 15, 2013, 3 pages.
Nicolas, H. et al. "Cucurbit[8]uril as Nanocontainer in a Polyelectrolyte Multilayer Film: A Quantitative and Kinetic Study of Guest Uptake," Langmuir 2015, 31, 10734-10742. Published: Sep. 15, 2015 (Year: 2015).
Rouhani, S. et al. "Molecular imprinting-based fluorescent optosensor using a polymerizable 1,8-naphthalimide dye as a florescence functional monomer," Sensors and Actuators B 197 (2014) 185-192 (Year: 2014).
Sekowski, J et al. "Biotic-abiotic interfaces within a nanostructured polymer matrix platform: towards a completely abiotic system," ECBC FY10 ILIR Technical Report Executive Review (2010): 19, 6 pages (Year: 2010).
Sellergren, B. et al. "Layer-by-Layer Grafting of Molecularly Imprinted Polymers via Iniferter Modified Supports," Adv. Mater. 14, 17 (2002) 1204-1208. (Year: 2002).
Sharma, Piyush Sindhu et al., "Surface development of molecularly imprinted polymer films to enhance sensing signals", Trends in Analytical Chemistry, vol. 51, Nov. 1, 2013, pp. 146-157.
Taolei Sun et al., "Functional biointerface materials inspired from nature", The Royal Society of Chemistry 2011, Chem. Soc. Rev., 2011, 40, 2909-2921.
Tan, Shawn J et al., "Plasmonic Color Palettes for Photorealistic Printing with Aluminum Nanostructures", Nano Letters 2014, 14, pp. 4023-4029.
Tokareva, Iryna et al., "Ultrathin molecularly imprinted polymer sensors employing enhanced transmission surface plasmon resonance spectroscopy" The Royal Society of Chemistry Chem. Commun., (Received Apr. 4, 2006; accepted Jun. 20, 2006; published online Jun. 30, 2006), pp. 3343-3345.
Tokonami, Shiho et al., "Review: Micro- and nanosized molecularly imprinted polymers for highthroughput analytical applications", Analytica Chimica Acta, vol. 641, 2009, pp. 7-13.
Wang, Yifei et al., "Strain-tunable plasmonic crystal using elevated nanodisks with polarization-dependent characteristics", Applied Physics Letters 108, 071110, (Received Nov. 19, 2015; accepted Feb. 9, 2016; published online Feb. 19, 2016), 5 pages.
Yue, Y. et al. "Tunable one-dimensional photonic crystals from soft materials," Journal of Photochemistry and Photobiology C: Photochemistry Reviews 23 (2015) 45-67. Available online May 5, 2015 (Year: 2015).
Yuting Xiong et al., "Sialic acid-triggered macroscopic properties switching on a smart polymer surface", Applied Surface Science 427 (2018) 1152-1164.
Zhang Z, Liu J. Molecular Imprinting with Functional DNA. Small. Jun. 2019; 15(26): e1805246. doi: 10.1002/smll.201805246. Epub Feb. 13, 2019. PMID: 30761744. (Year: 2019).
International Search Report and Written Opinion for International Application No. PCT/US2017/056553, mailed Dec. 22, 2017, 12 pages.
Australian Examination Report No. 1 for Australian Application No. 2017342463, dated Sep. 10, 2021, 3 pages.
Notice of Acceptance for Australian Application No. 2017342463, dated Sep. 1, 2022, 3 pages.
Intent to Grant for European Application No. 17797477.1 dated Sep. 28, 2022, 82 pages.
Non-Final Office Action for U.S. Appl. No. 16/381,436 dated Sep. 22, 2021, 17 pages.
Notice of Allowance for U.S. Appl. No. 16/381,436 dated Mar. 31, 2022, 10 pages.
Corrected Notice of Allowability for U.S. Appl. No. 16/381,436 dated Jul. 19, 2022, 5 pages.
Non-Final Office Action for U.S. Appl. No. 17/868,604 dated Dec. 21, 2022, 23 pages.
Final Office Action for U.S. Appl. No. 17/868,604 dated Apr. 3, 2023, 9 pages.
Notice of Allowance for U.S. Appl. No. 17/868,604 dated Jul. 10, 2023, 10 pages.
Corrected Notice of Allowability for U.S. Appl. No. 17/868,604 dated Aug. 31, 2023, 11 pages.
Non-Final Office Action for U.S. Appl. No. 18/488,463 dated Feb. 14, 2025, 20 pages.
Final Office Action for U.S. Appl. No. 18/488,463 dated Jun. 18, 2025, 23 pages.
Notice of Allowance for U.S. Appl. No. 18/488,463 dated Jul. 11, 2025, 8 pages.

* cited by examiner

Color 1

Color 2

350
114
355

360
350
365
355
300

400
401
401
z
x
y 400
401
410
z
x
y 402
405
403
401

400
401
403
410
401
401
405
z
x
y

Figure 11:
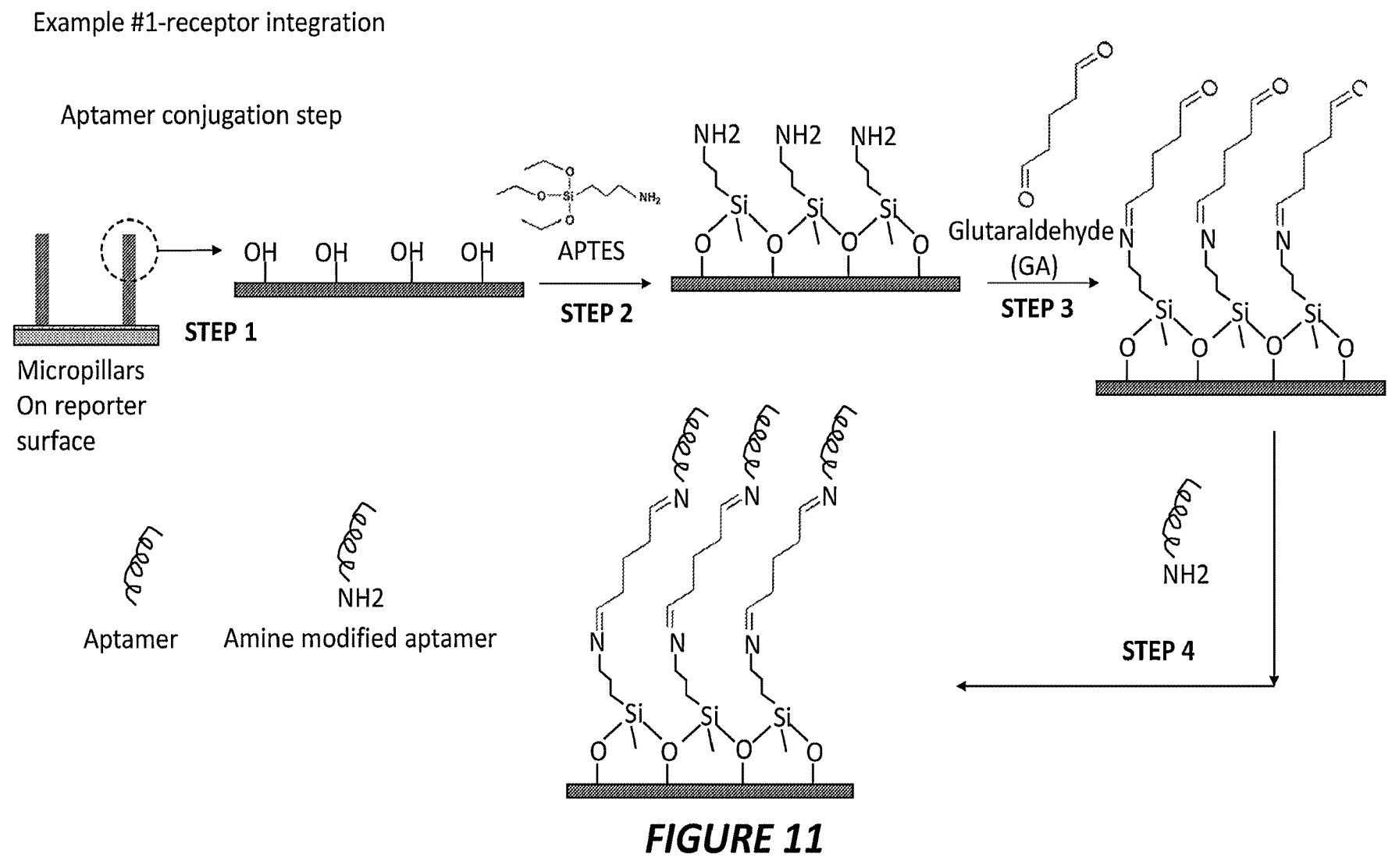

Example #1-receptor integration

Aptamer conjugation step

Micropillars On reporter surface

STEP 1

OH OH OH OH

APTES

STEP 2

NH2 NH2 NH2

Glutaraldehyde (GA)

STEP 3

NH2

STEP 4

Aptamer

Amine modified aptamer

DEVICES AND METHODS FOR DETECTING A TARGET ANALYTE OF INTEREST

CROSS-REFERENCE TO RELATED APPLICATION

This application is a National Stage Entry of PCT Application Serial No. PCT/US2021/44403, filed on Aug. 3, 2021, which claims priority to U.S. Provisional Patent Application No. 63/060,597, which was filed on Aug. 3, 2020. The disclosures and contents of the above-referenced applications are incorporated by reference in their entireties for all purposes.

FIELD OF THE INVENTION

In general, in various embodiments, the present invention relates to devices and methods for the detection of analytes in a fluid (e.g., liquid) sample. More specifically, the devices and methods have a high affinity for an analyte, are capable of detecting analytes in low concentrations, such as protein biomarkers, drugs, or toxins, and provide a (e.g., optical) signal as a notification to an end user upon detection.

BACKGROUND OF THE INVENTION

The ability to rapidly detect trace amounts of analytes without the need for complicated or expensive equipment and without highly trained technicians is a capability that is highly sought across multiple industries, including health care, agriculture, environmental, defense, law enforcement, and many others.

Point-of-care (POC) diagnostics, in particular, are one of the fastest growing markets in life sciences, with the benefits including quick and efficient testing and the abilities to reach more patients, eliminate follow-up visits, and ultimately save money and lives in the healthcare system. POC diagnostics have many direct applications in hospital systems, pharmacies, critical care settings, mobile settings, and resource-limited settings.

Current state of the art techniques include the enzyme-linked immunoassay (ELISA), lateral flow immunoassay (LFA), and ribonucleic acid (RNA) based diagnostics, such as real-time reverse transcription polymerase chain reaction (RT-PCR). Most ELISA and RNA tests, however, are not truly POC formats, as they require specialized laboratories with extraordinary resources and staffed with highly trained technicians to run the tests and interpret the results. Even RNA tests touted as POC require PCR amplification and a hand-held electrical device for signal readout and interpretation, making such tests far from practical for widespread usage. As for LFAs, even though they require a POC format, they often come with reliability issues, lack in robustness and, moreover, often are limited to applications that utilize antibodies.

Therefore, a need exists across several fields for a novel, rapid, easy to use, and reliable analyte detection device.

SUMMARY OF THE INVENTION

In general, in a first aspect, embodiments of the invention relate to a sensor for detecting an analyte of interest in a fluid sample. In some embodiments, the sensor includes (i) a structure having a plurality of surficial walls and (ii) a binding material that binds the analyte of interest. In some implementations, the surficial walls of the structure define a plurality of air gaps in the structure and the binding material is present on the surficial walls. In some applications, the structure may be configured such that both a fluid sample lacking the analyte of interest and a fluid sample containing the analyte of interest are initially able to penetrate the plurality of air gaps. Advantageously, the sensor may be configured such that, when the analyte of interest binds to the binding material, a change in surface energy results within the surficial walls.

In some implementations, the change in surface energy that results within the surficial walls prevents the fluid sample containing the analyte of interest from exiting the air gaps. In other implementations, the change in surface energy that results within the surficial walls allows the fluid sample containing the analyte of interest to exit the air gaps.

In some applications, the sensor may also include a plurality of first structural elements coupled to at least one surficial wall. The at least one surficial wall may have a first order dimension, while the first structural elements may have a second order dimension of lower order than the first order dimension. Optionally, a plurality of second structural elements may be coupled to at least one first structural element. The plurality of second structural elements may have a third order dimension of lower order than the second order dimension. In one variation, the first order dimension may have a micrometer scale and the second order dimension may have a nanometer scale. In another variation, the first order dimension may have a millimeter scale, the second order dimension may have a micrometer scale, and the third order dimension may have a nanometer scale.

In some embodiments, the binding material comprises or defines a binding agent that binds an analyte of interest. The binding material can be selected from the group consisting of a molecularly-imprinted polymer (MIP) material, aptamer, slow off-rate modified aptamer (SOMAmer), affimer, protein (e.g., antibody), glycoprotein, peptide, nucleic acid (e.g., deoxyribonucleic acid (DNA) and ribonucleic acid (RNA)), peptide nucleic acid (PNA), oligonucleotide, coordination complex, metal organic framework (MOF) material, porous coordination polymer material, and combinations thereof. In some variations, the binding material is at least one of: produced from hydrophobic components, produced from hydrophilic components that are coated with a hydrophobic layer, or combinations thereof. In other variations, the binding material may also include a specific binding enhancement layer and/or an additional layer to reduce non-specific binding from non-target substances contained in the fluid sample.

In further implementations, the sensor may include one or more of: a plurality of polymer brushes coupled to the plurality of surficial walls, a hydrophobic material coated on the plurality of surficial walls, and/or a colorimetric indicator. In some implementations, the surficial walls of the structure are roughened.

In general, in a second aspect, embodiments of the invention relate to a method for detecting an analyte of interest in a fluid sample. In some embodiments, the method includes contacting a sensor with a fluid sample and determining whether the fluid sample includes the analyte of interest by observing the sensor. The sensor may include (i) a structure having a plurality of surficial walls and (ii) a binding material that binds the analyte of interest. In some implementations, the surficial walls of the structure define a plurality of air gaps in the structure and the binding material is present on the surficial walls. In some applications, the structure may be configured such that both a fluid sample lacking the analyte of interest and a fluid sample containing the analyte of interest are initially able to penetrate the plurality of air gaps. Advantageously, the sensor may be configured such that, when the analyte of interest binds to the binding material, a change in surface energy results within the surficial walls.

In some implementations, the change in surface energy that results within the surficial walls prevents the fluid sample containing the analyte of interest from exiting the air gaps. In other implementations, the change in surface energy that results within the surficial walls allows the fluid sample containing the analyte of interest to exit the air gaps. In some applications, determining whether the fluid sample includes the analyte of interest may involve observing a color exhibited by the sensor and/or observing whether or not the fluid sample is prevented from exiting the air gaps.

In some embodiments, the sensor may also include a plurality of first structural elements coupled to at least one surficial wall. The at least one surficial wall may have a first order dimension, while the first structural elements may have a second order dimension of lower order than the first order dimension. Optionally, a plurality of second structural elements may be coupled to at least one first structural element. The plurality of second structural elements may have a third order dimension of lower order than the second order dimension. In one variation, the first order dimension may have a micrometer scale and the second order dimension may have a nanometer scale. In another variation, the first order dimension may have a millimeter scale, the second order dimension may have a micrometer scale, and the third order dimension may have a nanometer scale.

In some implementations, the binding material comprises or defines a binding agent that binds an analyte of interest. The binding material can be selected from the group consisting of a molecularly-imprinted polymer (MIP) material, aptamer, slow off-rate modified aptamer (SOMAmer), affimer, protein (e.g., antibody), glycoprotein, peptide, nucleic acid (e.g., deoxyribonucleic acid (DNA) and ribonucleic acid (RNA)), peptide nucleic acid (PNA), oligonucleotide, coordination complex, metal organic framework (MOF) material, porous coordination polymer material, and combinations thereof. In some variations, the binding material is at least one of: produced from hydrophobic components, produced from hydrophilic components that are coated with a hydrophobic layer, or combinations thereof. In other variations, the binding material further includes a specific binding enhancement layer and/or an additional layer to reduce non-specific binding from non-target substances contained in the fluid sample.

In further implementations, the sensor may include one or more of: a plurality of polymer brushes coupled to the plurality of surficial walls, a hydrophobic material coated on the plurality of surficial walls, and/or a colorimetric indicator. In some applications, the surficial walls of the structure may be roughened.

BRIEF DESCRIPTION OF THE DRAWINGS

In the drawings, like reference characters generally refer to the same parts throughout the different views. For the purposes of clarity, not every component may be labeled in every drawing. Also, the drawings are not necessarily to scale, emphasis instead generally being placed upon illustrating the principles of the invention. In the following description, various embodiments of the present invention are described with reference to the following drawings, in which:

FIG. 1A shows a sensor with a wetting mode-based colorimetric sensing mechanism having a "non-sticky" Wenzel state, in accordance with some embodiments of the present invention;

FIG. 1B shows a fluid that does not contain a target analyte of interest rolling off a structure in a "non-sticky" Wenzel state, in accordance with some embodiments of the present invention;

FIG. 1C shows a sensor with a wetting mode-based colorimetric sensing mechanism having a "sticky" Wenzel state, in accordance with some embodiments of the present invention;

FIG. 1D shows a fluid that contains a target analyte of interest adhering to or being adsorbed by a structure in a "sticky" Wenzel state, in accordance with some embodiments of the present invention;

FIG. 11 shows a schematic of an exemplary method of conjugating an aptamer to a sensor surface via glutaraldehyde crosslinking, in accordance with some embodiments of the present invention;

DETAILED DESCRIPTION

Figure 2B:
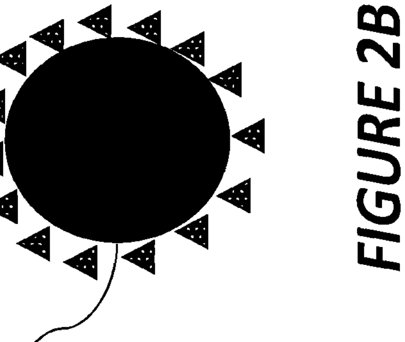
FIGS. 2A and 2B show illustrative hierarchical structures for a transducer, in accordance with some embodiments of the present invention.

To provide an overall understanding of the invention, certain illustrative embodiments will now be described, including devices, methods of making the devices, and methods of detecting an analyte target molecule of interest in a fluid sample. However, the devices and methods described herein may be adapted and modified as appropriate for the application being addressed and the devices and methods described herein may be employed in other suitable applications. All such adaptations and modifications are to be considered within the scope of the invention.

Throughout the description, where compositions and devices such as a sensor are described as having, including, or comprising specific components, or where processes and methods are described as having, including, or comprising specific steps, it is contemplated that, additionally, there are compositions and devices of the present disclosure that consist essentially of, or consist of, the recited components, and that there are processes and methods according to the present disclosure that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a device or a method described herein can be combined in a variety of ways without departing from the spirit and scope of the present disclosure, whether explicit or implicit herein. For example, where reference is made to a particular feature, that feature can be used in various embodiments of the devices of the present disclosure and/or in methods of the present disclosure, unless otherwise understood from the context. In other words, within this application, embodiments have been described and depicted in a way that enables a clear and concise application to be written and drawn, but it is intended and will be appreciated that embodiments can be variously combined or separated without parting from the present teachings and disclosure. For example, it will be appreciated that all features described and depicted herein can be applicable to all aspects of the disclosure described and depicted herein.

The articles "a" and "an" are used in this disclosure to refer to one or more than one (i.e., to at least one) of the grammatical object of the article, unless the context is inappropriate. By way of example, "an element" means one element or more than one element.

The term "and/or" is used in this disclosure to mean either "and" or "or" unless indicated otherwise.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present disclosure also includes the specific quantitative value itself, unless specifically stated otherwise. As used herein, the term "about" refers to a ±10% variation from the nominal value unless otherwise indicated or inferred.

Where a percentage is provided with respect to an amount of a component or material in a composition such as a polymer, the percentage should be understood to be a percentage based on weight, unless otherwise stated or understood from the context.

Where a molecular weight is provided and not an absolute value, for example, of a polymer, then the molecular weight should be understood to be an average molecule weight, unless otherwise stated or understood from the context.

It should be understood that the order of steps or order for performing certain actions is immaterial so long as the present disclosure remains operable. Moreover, two or more steps or actions can be conducted simultaneously.

At various places in the present specification, features are disclosed in groups or in ranges. It is specifically intended that the description include each and every individual sub-combination of the members of such groups and ranges. For example, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20.

The use of any and all examples, or exemplary language herein, for example, "such as" or "including," is intended merely to illustrate better the present disclosure and does not pose a limitation on the scope of the disclosure unless claimed. No language in the specification should be construed as indicating any non-claimed element as essential to the practice of the present disclosure.

Various aspects of the disclosure are set forth herein under headings and/or in sections for clarity; however, it is understood that all aspects, embodiments, or features of the disclosure described in one particular section are not to be limited to that particular section but rather can apply to any aspect, embodiment, or feature of the present disclosure.

Wetting Mode-Based Sensing

Two wetting modes can exist when a fluid (e.g., liquid) interacts with a hydrophobic solid surface. Cassie mode is known to prevent fluid (e.g., liquid) from penetrating into air gaps by forming a solid-liquid-air interface, so that the liquid is extremely mobile (i.e., "non-sticky") and can roll freely on the solid surface when the solid surface is tipped or flipped. Wenzel mode is another wetting mode in which the fluid (e.g., liquid) penetrates into the air gaps of a structured surface, which enables the fluid (e.g., liquid) to fully wet the surface of the structure and become immobile (i.e., "sticky") on the solid surface. In the following text, "non-sticky" may be used as an interchangeable term with "slippery" to indicate a slippery state describing the mobile nature of a liquid on a designed surface when the surface is tilted or flipped, while "sticky" may be used interchangeably with "wet" to indicate a wet state of the liquid in which the liquid adheres to or is adsorbed by the solid surface, preventing the liquid from running off of the solid surface when it is tilted or flipped. The physical origin of the "sticky" Wenzel mode is liquid pinning, which results from the interaction of liquid with the solid surface.

The in-flow and/or presence of a specific fluid, e.g., a fluid containing a target analyte of interest, in the air gaps/voids of a three-dimensional ("3D") structure may be used in diagnostic devices, e.g., photonic crystals and other colorimetric sensors, to verify or confirm the presence of the specific fluid. Indeed, and more particularly, a color change detectable in the visible spectrum of light refracted by the structure due to, inter alia, a difference in the refractive index of the structure because of the presence of the fluid in the air gaps/voids may be used to identify the nature of the fluid captured in the air gaps of the structure. In this type of sensor device, the sensing mechanism is based on a Cassie-to-Wenzel transition. More specifically, the initial wetting state may be a Cassie mode that prevents liquid from infiltrating into air gaps/voids, while the end wetting state upon analyte binding may be a Wenzel mode that allows liquid to infiltrate the air gaps/voids and adhere to or be adsorbed by the surface.

However, in some other implementations, it is possible to design a sensor that has a transition from a "non-sticky" Wenzel mode (a mode in which liquid is able to penetrate into the air gaps/voids of the 3D structure but the structure remains non-sticky) to a "sticky" Wenzel mode. In such implementations, the initial "non-sticky" Wenzel wetting state allows all liquids to penetrate the air gaps/voids; however, a liquid lacking an analyte of interest can roll off or be poured off the structure, reverting the surface of the structure to a dry state with no liquid in the air gaps/voids. In short, the liquid lacking the analyte of interest is incapable of sticking to the structure; hence, "non-sticky." In the presence of a liquid containing a target analyte of interest, however, the end wetting state is a "sticky" Wenzel mode in which the liquid containing the target analyte of interest is retained in the air gaps/voids after removal of the sensor from the liquid sample.

According to some embodiments of the present invention, the in-flow and/or presence of a specific fluid, such as a fluid containing a target analyte of interest (e.g., fuel containing contaminants, blood or saliva containing certain biomarkers for certain diseases or injuries, liquid containing certain drugs, and the like), may be detected using wetting-based colorimetric devices having colorimetric (e.g., dye, pigment, photonic crystal, and the like) indicators that are structured and arranged to exhibit an observable change in color upon contact with the fluid and the fluid adhering to, attaching to, and/or being adsorbed by the surface of the structure.

Figures 1A, 1B, 1C, 1D:
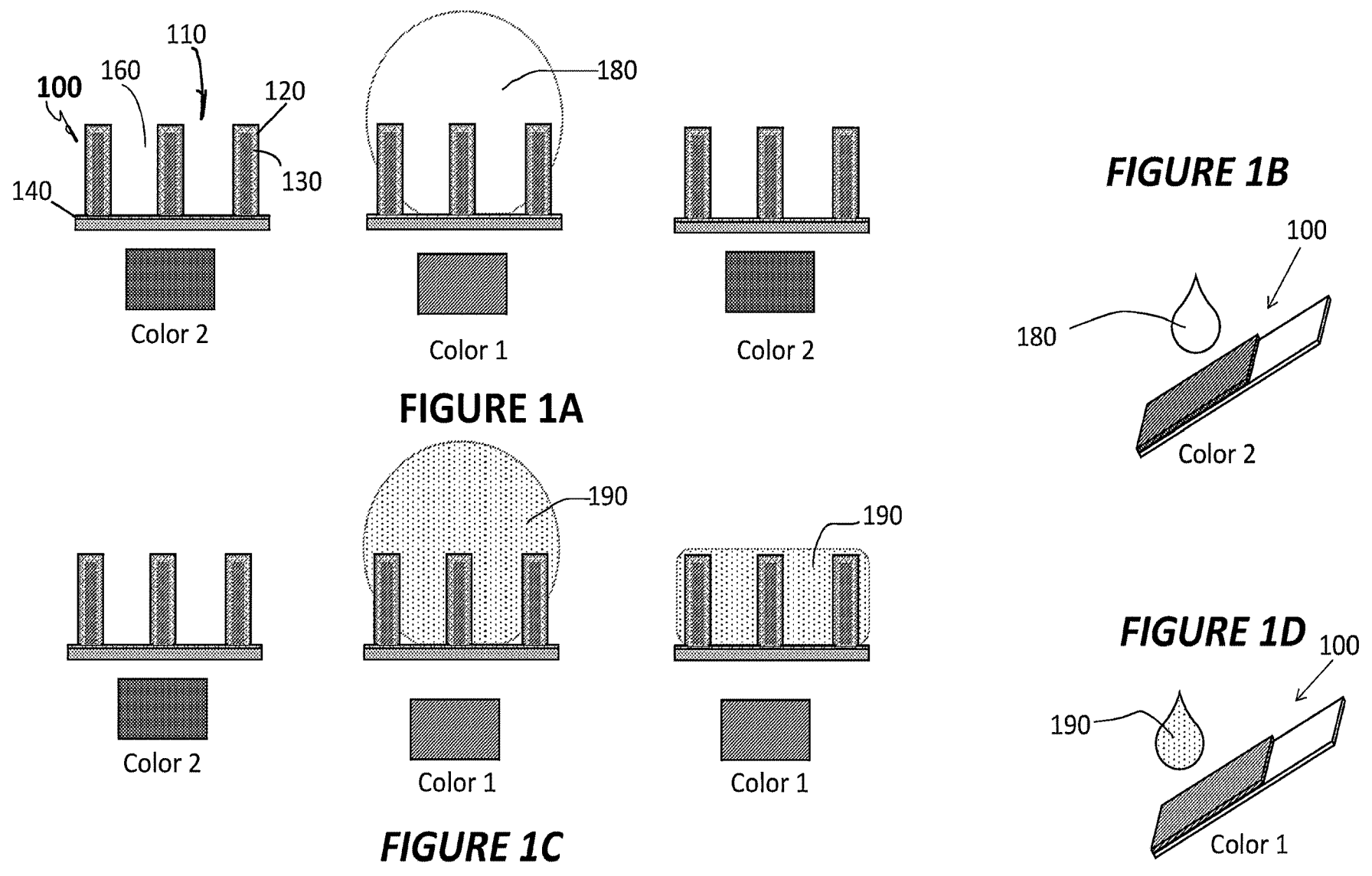

Referring to FIGS. 1A-1D, an exemplary first embodiment of a wetting-based colorimetric sensing device, or sensor, 100 is shown. In particular, the sensor 100 is one that, as further described below, transitions from a "non-sticky" Wenzel mode to a "sticky" Wenzel mode when an analyte of interest is present in a fluid. As shown in FIG. 1A, in some implementations, the three-dimensional ("3D") sensor or sensing device 100 may include a transducer 110 and an indicator 140 (e.g., a colorimetric indicator 140) that are physically spaced from one another. In some applications, the transducer 110 may include a plurality of microstructures and/or nanostructures 120 (e.g., pillars, micropillars, nanopillars, and the like) having air voids and/or gaps 160 between adjacent microstructures and/or nanostructures 120.

In some implementations, the (e.g., 3D) transducer 110 may include a roughened surface comprising microscale and/or nanoscale features. The microscale and nanoscale features may include microstructures or nanostructures 120 (e.g., a plurality of pillars, micropillars, or nanopillars) or combination of both. In some applications, the microstructures and/or nanostructures 120 (e.g., pillars, micropillars, and/or nanopillars) may be manufactured of a dielectric or insulative material (e.g., silica, titanium dioxide, silicon nitride, and the like), a (e.g., organic, inorganic, or hybrid) molecularly-imprinted polymer (MIP) material, a metallic material (e.g., gold, silver, aluminum, and the like), a metallic material coated with a MIP material, and combinations thereof.

In some embodiments, the surface of the microstructures and/or nanostructures 120 (e.g., pillars, micropillars, and/or nanopillars) may be coated with a (e.g., thin) layer of a binding material 130 (e.g., analyte receptor), such as aMIP material, aptamer material, slow off-rate modified aptamer (SOMAmer), affimer, protein (e.g., antibody), glycoprotein, peptide, nucleic acid (e.g., deoxyribonucleic acid (DNA) and ribonucleic acid (RNA)), peptide nucleic acid (PNA), oligonucleotide, coordination complex, metal organic framework (MOF) material, porous coordination polymer material, and so forth, or combinations thereof. In some implementations, the thickness of the binding material (e.g., analyte receptor) coating 130 may range from about 1 Angstrom (e.g., in the case of a molecular monolayer) to about a thickness of approximately the distance between the adjacent microstructures and/or nanostructures 120 (e.g., the plurality of pillars, micropillars, and/or nanopillars). Advantageously, the binding material (e.g., analyte receptor) coating 130 may also include a binding material produced from hydrophobic components, so that the binding material is hydrophobic, or produced from hydrophilic binding materials coated with an additional hydrophobic layer, or combinations thereof. In some implementations, the binding material (e.g., analyte receptor) coating 130 may also include a specific binding enhancement layer or an additional layer to reduce non-specific binding from non-target substances in the liquid. Non-limiting examples of such a layer include polymer brushes, zwitterionic polymers, protein blocker agents and so forth.

The transducer 110 and indicator 140 may be structured and arranged to verify or confirm the presence (or absence) of a specific fluid (e.g., a fluid containing the target analyte of interest). For example, as shown in FIG. 1A, when a fluid 180 that does not contain the target analyte of interest contacts the surface of the sensor 100, the fluid 180 initially penetrates the air gaps/voids 160 disposed between the plurality of microstructures and/or nanostructures 120 in the transducer 110. The presence of the fluid 180 in the air gaps/voids 180 modifies the refractive index of the sensor 100, thus leading to an observable color change. In particular, the penetration of the fluid 180 into the air gaps/voids 160 when the sensor 100 is exposed to the fluid 180 may, initially, cause the sensor 100 to exhibit a different color (designated "Color1" in FIG. 1A) from the original color (designated as "Color2" in FIG. 1A) exhibited by the sensor 100 in air or ambient conditions (namely, when the fluid 180 is absent).

Since, however, the fluid 180 does not contain the target analyte of interest, sensor 100 remains in a "non-sticky" Wenzel wetting mode. As a result, the fluid 180 can roll off the surface of the sensor 100 when the sensor 100 is tilted or flipped. The absence (e.g., runoff) of the fluid 180 returns the sensor 100 to its original color ("Color2"), thereby providing indicia of an absence of the target analyte of interest in the fluid 180. FIG. 1B shows this phenomena schematically—e.g., tilting or flipping the sensor 100 causes the fluid 180 that does not contain a target analyte of interest to roll off the sensor 100, thereby causing the sensor 100 to exhibit its original color ("Color2").

As shown in FIG. 1C, when a fluid 190 that contains the target analyte of interest contacts the surface of the sensor 100, it too initially penetrates the air gaps/voids 160 between the microstructures and/or nanostructures 120 of the transducer 110. The target analytes of interest present in the fluid 190 proceed to bind with the binding material 130 (e.g., the analyte receptor). The binding of the target analytes of interest to the binding material 130 leads to a change in the surface energy within the surficial walls of the microstructures and/or nanostructures 120, a wetting of those surficial walls, and a transition of the sensor 100 to a "sticky" Wenzel state. As before, the presence of the fluid 190 in the air gaps/voids 160 modifies the refractive index of the sensor 100, thus leading to an observable color change. In particular, the penetration of the fluid 190 into the air gaps/voids 160 when the sensor 100 is exposed to the fluid 190 may cause the sensor 100 to exhibit a different color (designated "Color1" in FIG. 1C) from the original color (designated as "Color2" in FIG. 1C) exhibited by the sensor 100 in air or ambient conditions (when the fluid 190 is absent).

The "sticky" Wenzel state of the sensor 100 created by the binding of the target analytes of interest in the fluid 190 to the binding material 130 (e.g., the analyte receptor) prevents the fluid 190 from rolling off the surface of the sensor 100 when the sensor 100 is tilted or flipped (e.g., the fluid 190 remains trapped within the air gaps/voids 160 between the microstructures and/or nanostructures 120 of the transducer 110). Accordingly, the sensor 100 maintains the different color (designated "Color1" in FIG. 1C) and does not return to its original color (designated "Color2" in FIG. 1C) even when the sensor 100 is tilted or flipped, thereby providing indicia of the presence of the target analytes of interest in the fluid 190. FIG. 1D shows this phenomena schematically—e.g., tilting or flipping the sensor 100 does not cause the fluid 190 that contains the target analytes of interest to roll off the sensor 100, thereby causing the sensor 100 to exhibit a color ("Color1") different from its original color ("Color2").

Although FIGS. 1A-1D show a pillar-based micro- and/or nanostructure sensor 100 having three microstructures and/or nanostructures 120, that is done for the purpose of illustration rather than limitation. Indeed, any number of microstructures and/or nanostructures 120 (e.g., micro- and/or nanopillars), any shape of microstructures and/or nanostructures 120, and any arrangement or distribution of microstructures and/or nanostructures 120 on the surface of the indicator 140 may be used. For example, the microstructures and/or nanostructures 120 may be micro- and/or nanopillars formed in a periodic, aperiodic, and/or random array. Furthermore, the microstructures and/or nanostructures 120 may be separated from each other to form a single air gap/void or a plurality of air gaps/voids 160.

Separation distances between (e.g., adjacent) microstructures and/or nanostructures 120 may be as close as about 0.1 nanometers ("nm"). In some variations, the separation distance may be in the range from 0.1 nm to 10,000 microns. In another exemplary embodiment, rather than micro- and/or nanopillars 120, the transducer 110 may include, for the purpose of illustration rather than limitation: microspheres, nanospheres, microparticles, nanoparticles, micro-scaled islands (e.g., discontinuous features on a thin film) and/or nano-scaled islands configured with any other shapes or irregular shapes and/or an aggregation of these structures and/or combination thereof. Furthermore, these microstructures and/or nanostructures 120 may be separated from each other to form a plurality of air gaps/voids 160.

In some implementations, the width (e.g., rectangular shaped) or the diameter (e.g., circular shaped) and the height of the micropillars and/or nanopillars 120 may range from about 0.001 nm to about 10,000 microns. Those skilled in the art can appreciate that selection of the size (e.g., diameter or other dimension) of the micropillars and/or nanopillars 120 may depend on the target analyte of interest; hence, the size of the micropillars and/or nanopillars 120 may be smaller than 0.001 nm or larger than 10,000 microns. Moreover, although the (e.g., circular) micropillar and/or nanopillar diameters and/or (e.g., rectangular) micropillar and/or nanopillar widths shown in FIGS. 1A-1D appear to be uniform in dimension, that, too, is done for the purpose of illustration rather than limitation. Indeed, in some variations, a variety of micropillar and/or nanopillar diameters or other dimensions may be formed on a single sensing device 100. As one non-limiting example, a hierarchical structure of microstructures and/or nanostructures 120 with two or more size dimensions may be formed.

Figures 25A, 25B:
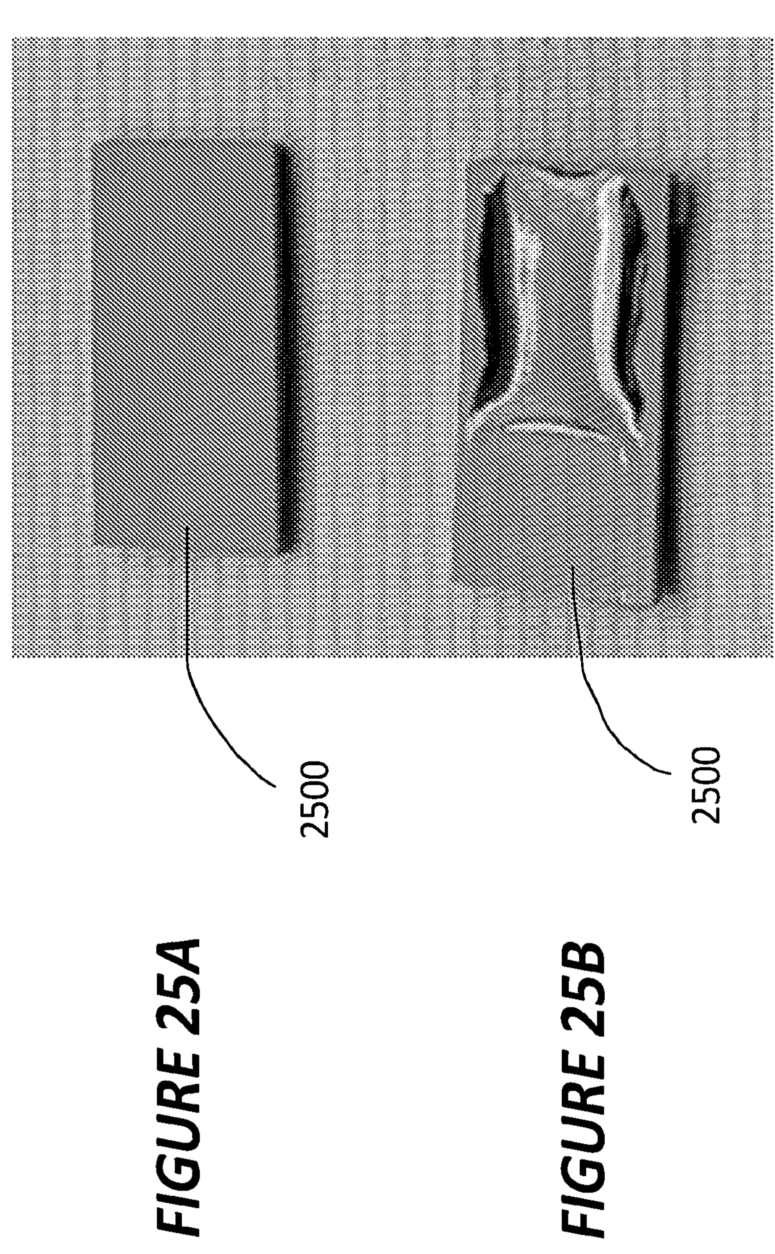
FIGS. 25A and 25B show signal readout from visually-flat surfaces developed to detect beta-2-transferrin protein that, respectively, do not include a target analyte of interest and include a target analyte of interest, in accordance with some embodiments of the present invention.

In some other non-limiting examples, the surface of the sensor 100 may be a roughened surface that comprises random vertical deviations of a roughness profile from a mean line. The vertical deviation may range from about 0.001 nm to about 10,000 microns. Those of ordinary skill in the art can appreciate that, in some applications, the vertical deviation may be smaller than 0.001 nm or larger than 10,000 microns. When the surface roughness is below the visible optical wavelength (e.g., below 380 nm), the surface may visually appear to be flat to human eyes, as shown in FIGS. 25A and 25B.

In some implementations, to prevent or limit fluids 180 that do not contain a target analyte of interest from becoming trapped within the air gaps/voids 160 between the microstructures and/or nanostructures 120 of the transducer 110, a hydrophobic material (e.g., Teflon, silane, and the like) may be coated on the surficial walls of the microstructures and/or nanostructures 120. Advantageously, the hydrophobic coating may be designed to repel all fluids 180 that do not contain the target analyte of interest, thereby allowing the fluid 180 to roll off the surface of the sensing device 100 and preventing the fluid 180 from becoming trapped within the air gaps/voids 160 between the microstructures and/or nanostructures 120. Those of ordinary skill in the art can appreciate that, in some applications, the microstructures and/or nanostructures 120 may be coated with a hydrophobic material as well as with the binding material 130 (e.g., an analyte receptor).

In some embodiments, the colorimetric indicator 140 is structured and arranged to exhibit a color change when a fluid is in contact with and/or sticking to (e.g., attached to, adhered to, adsorbed by, and the like) the surface of the colorimetric indicator 140. In some embodiments, the colorimetric indicator 140 is a structural color indicator. Exemplary structural color indicators include Bragg reflective coatings, photonic crystals, and interference-based thin film reflectors, and the like. The detectable visible color difference (i.e., the change of color) that results from liquid interaction with a structural color indicator is generally referred to as a structural color change. As one non-limiting example, there may be a color change in the visible spectrum of light refracted by the colorimetric indicator 140 once the fluid is introduced into (e.g., photonic crystals associated with) the colorimetric indicator 140. In other words, the introduction of the fluid may lead to a difference in the refractive index of the colorimetric indicator 140. Advantageously, the difference in the refractive index may be used to identify the nature of the fluid trapped within the air gaps/voids 160.

Another suitable structural color indicator may be, for example, a thin film of dielectric/metallic/semiconductor material deposited on another dielectric/metallic/semiconductor material (e.g., a silicon oxide thin film deposited on silicon, gold, or germanium deposited on silicon).

In some implementations, the sensing device 100 may be used without the colorimetric indicator 140. For example, a fluid sticking to the surface of the sensing device 100 may be visualized upon the binding of target analytes of interest with the binding material 130 (e.g., an analyte receptor). A fluid that cannot roll off the surface of the sensing device 100 may be directly visualized by the naked human eye. Furthermore, the sensing device 100 may also be used without the microstructures and/or nanostructures 120 (e.g., pillars, micropillars, nanopillars, and the like) or colorimetric indicator 140. For example, a fluid sticking to a flat and smooth surface may be visualized upon the binding of a target analyte of interest with the binding material 130 (e.g., an analyte receptor) of the sensing device 100. More specifically, a fluid that cannot roll off the surface of the sensing device 100 may be directly visualized by the naked human eye.

Figure 2A:
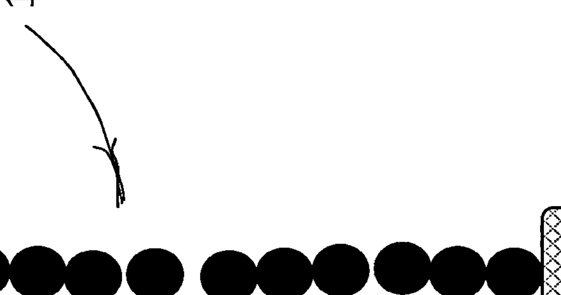
Figure 2A:
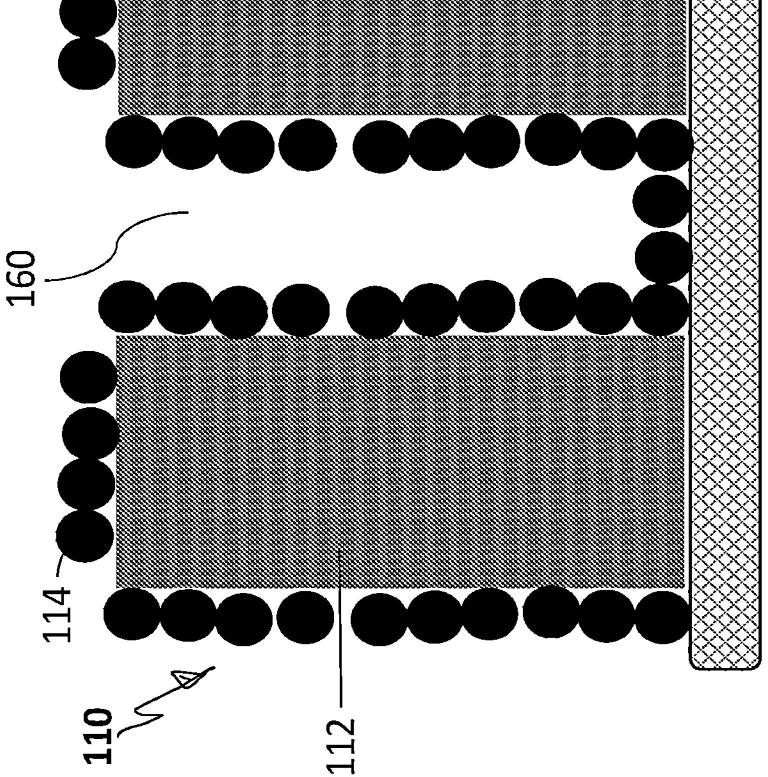

Referring to FIGS. 2A and 2B, an illustrative embodiment of a transducer 110 with hierarchical structure, which refers to structural elements which in turn also have structures in a size hierarchical manner, is shown. For the purpose of illustration rather than limitation, the transducer 110 may be similar to (and be implemented in a similar fashion to) the transducer 110 previously described with reference to FIGS. 1A-1D. In other words, the previous description of the transducer 110 is equally applicable to the transducer 110 shown in FIGS. 2A and 2B.

In some embodiments, the hierarchical structure includes two or more than two orders of structural dimensions. An exemplary hierarchical may include a nanometer-scaled structure 114 (e.g., nanospheres and the like) on top of a micrometer-scaled structure 112 (e.g., micropillars and the like). Furthermore, in some variations, more than two (e.g., three) orders of dimension may be used. For example, instead of being a micrometer-scaled structure, structure 112 may be a millimeter-scaled structure (e.g., a pillar and the like) while, instead of being a nanometer-scaled structure, structure 114 may be on the order of micrometer scale. In such variations, an additional structure 116 with nanometer scale may be added on top of structure 114. The spheres (in FIGS. 2A and 2B) and triangles (in FIG. 2B) are used for the purpose of illustration rather than limitation. Indeed, any number of microstructures and/or nanostructures, any shape of microstructures and/or nanostructures, and any arrangement or distribution of microstructures and/or nanostructures may be used.

The hierarchical structure is an important feature in making the Wenzel mode "not sticky." Fluid mobility on a surface is determined by the contact line pinning effect that results from the interaction of the fluid with nanoscale and/or sub-nanoscale features. For example, if the microscale pillars 112 are decorated with nanoscale features 114 (e.g., nanoparticles, nanobumps, nano-islands, and the like), the fluid may be (at the nanoscale) in a Cassie state—which is known to enable a highly mobile fluid on the surface—having nanoscaled air pockets trapped underneath the fluid. Although the fluid may be in a Wenzel mode in the microscale pillar 112 area and may penetrate into the air voids 160 between those microscale pillars 112, the fluid may still be highly mobile on such a microscale pillar 112 surface due to the Cassie mode at the nanoscale. If fluid that does not contain target analytes of interest comes in contact with the surface, the fluid is mobile on the surface (not sticky) due to the Cassie wetting mode at the nanometer scale. However, if fluid that does contain target analytes of interest contacts the surface, the target analytes of interest specifically bind to the surface and induce a Cassie-to- Wenzel transition at the nanometer scale, such that the fluid becomes sticky to the surface due to the contact line pinning.

In some applications, the nanometer-scaled features (e.g., nanospheres 114) coated with a hydrophobic layer may be used in conjunction with a flow shear (e.g., in a fluid flow) to reduce the non-specific binding of non-targets from a complex matrix. The nanometer scaled surface roughness creates an effective nanotribological system to reduce the friction, especially when the size of the target analytes of interest (e.g., proteins) is comparable to the roughness scale. If a fluid that does not contain target analytes of interest, but may contain other non-target confounders, comes into contact with the surface, the other non-target confounders may adhere to, become attached to, and/or be adsorbed by the surface non-specifically. This fluid, however, may still be washed off the surface, which enables fluid to become mobile on the surface (not sticky). In contrast, if fluid that does contain both target analytes of interest and other non-target confounders comes into contact with the surface, the target analytes of interest specifically bind to the surface and cannot be washed off the surface due to their tight binding affinity, which makes the fluid sticky to the surface because of a Cassie-to-Wenzel transition at the nanometer scale.

Figures 3A, 3B:
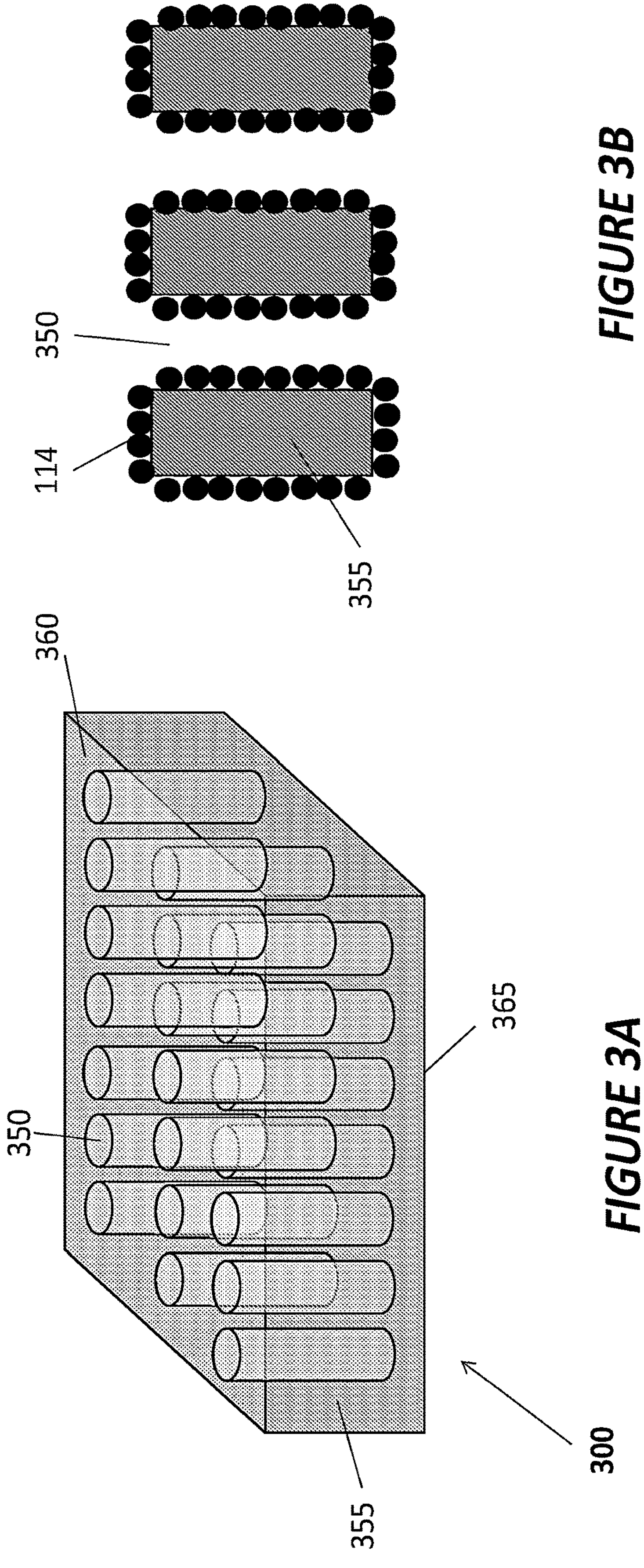
FIG. 3A shows a sensor having an array of (e.g., cylindrical) air gaps, in accordance with some embodiments of the present invention.
FIG. 3B shows an illustrative hierarchical structure for the sensor of FIG. 3A, in accordance with some embodiments of the present invention.

FIGS. 3A and 3B depict yet another embodiment of a sensor 300 that, as further described below, transitions from a "non-sticky" Wenzel mode to a "sticky" Wenzel mode when an analyte of interest is present in a fluid. The colorimetric sensor 300 may include a single or plurality of surfaces defining an array of (e.g., cylindrical or substantially cylindrical) air gaps/voids 350 (e.g., holes, microholes, nanoholes, and the like) in a base substrate 355. The base substrate 355 of the colorimetric sensor 300 may be made of an organic material, an inorganic material, or a hybrid organic and inorganic material; of a dielectric material, an insulative material, or a semiconductor material (e.g., silica, titanium dioxide, silicon nitride, silicon, and the like); of a metallic material (e.g., gold, silver, aluminum, and the like); or of any combination thereof. The cylindrical shape of the air gaps/voids 350 is for the purpose of illustration rather than limitation. Indeed, any number of air gaps/voids 350, any shape of air gaps/voids 350, and any arrangement or distribution of air gaps/voids 350 in a base substrate 355 may be used. For example, an inversed opal film (IOF) structure with spherically shaped air gaps/voids 350 may be employed. Although not shown in FIGS. 3A and 3B, the surficial walls defining the air gaps/voids 350 may be coated with a binding material 130 (e.g., an analyte receptor), as previously described. Alternatively, the base substrate 355 may itself be manufactured from a binding material (e.g., a molecularly imprinted polymer (MIP)), thereby obviating the need for the coating of the binding material 130.

Furthermore, additional structure with lower rank of dimensions (e.g., nanoparticles 114) may be coated on the surficial walls defining the air gaps/voids 350 to form a hierarchical structure as shown in FIG. 3B. The purpose of the hierarchical structure is to create a non-sticky Wenzel mode. The dimension of the air gaps/voids 350 may be in the range of nanometers to millimeters. For example, when the air gaps/voids 350 are in the millimeter scale, the lower rank feature 114 may be in the micrometer scale. In some applications, the "non-sticky" Wenzel mode may be activated by employing an external force (e.g., electrowetting, a mechanic pressure, and so forth). Although the (e.g., cylindrical or substantially cylindrical) air gaps/voids 350 (e.g., microholes, nanoholes, or the like) in FIG. 3A appear to extend from one face (e.g., the top face 360) of the base substrate 355 to a second face (e.g., the bottom face 365) of the base substrate 355, this is done for illustrative purposes only. In alternative embodiments, a first array of (e.g., cylindrical or substantially cylindrical) air gaps/voids 350 may be formed in the top face 360 and a second array of (e.g., cylindrical or substantially cylindrical) air voids 350 may be formed in the bottom face 365 of the base substrate 355, such that some portion of the base substrate 355 separates the bottoms of each of the (e.g., cylindrical or substantially cylindrical) air gaps/voids 350 formed in the top face 360 from the bottoms of each of the (e.g., cylindrical or substantially cylindrical) air gaps/voids 350 formed in the bottom face 365. In yet another variation, (e.g., cylindrical or substantially cylindrical) air gaps/voids 350 may be formed on other faces of the base substrate 355, in lieu of or including the top 360 and bottom faces 365.

Although pillar-based structures were used to describe the wetting property and analyte-binding induced wettability change in FIGS. 1A-1D, those of ordinary skill in the art can appreciate that the phenomenon of wettability may also be used in connection with air gap-based or hole-based structures including those having (e.g., cylindrical or substantially cylindrical) air gaps/voids 350, such as shown in FIGS. 3A and 3B. Indeed, when a fluid 180 that does not contain the target analyte of interest contacts the surface of the colorimetric sensor 300, it infiltrates into the air gaps/voids 350. As previously described, infiltration of the fluid 180 into the air gaps/voids 350 modifies the refractive index of the sensor 300, leading to an observable color change ("Color1") that differs from the initial color ("Color2") exhibited by the sensor 300 prior to infiltration of the fluid 180. However, because the fluid 180 does not contain the target analyte of interest, the colorimetric sensor 300 remains in a "non-sticky" Wenzel wetting mode. As a result, the fluid 180 can roll out of the (e.g., cylindrical or substantially cylindrical) air gaps 350 and off of the surfaces 360, 365 of the sensor 300 when the sensor 300 is tilted and/or flipped. The resulting absence of the fluid 180 in the (e.g., cylindrical or substantially cylindrical) air gaps 350 again modifies the refractive index of the sensor 300, returning the sensor 300 to its original color ("Color2"), thus providing indicia of an absence of the target analyte of interest in the fluid 180.

When a fluid 190 that contains the target analyte of interest comes into contact with the sensor 300, it also infiltrates all or part of the (e.g., cylindrical or substantially cylindrical) air gaps/voids 350. The target analytes of interest present in the fluid 190 proceed to bind with the binding material 130 (e.g., the analyte receptor). The binding of the target analytes of interest to the binding material 130 leads to a change in the surface energy within the surficial walls defining the air gaps/voids 350, a wetting of those surficial walls, and a transition of the sensor 300 to a "sticky" Wenzel state. As before, the presence of the fluid 190 in the air gaps/voids 350 modifies the refractive index of the sensor 300, thus leading to an observable color change. In particular, the penetration of the fluid 190 into the air gaps/voids 350 when the sensor 300 is exposed to the fluid 190 may cause the sensor 300 to exhibit a different color ("Color1") from the original color ("Color2") exhibited by the sensor 300 in air or ambient conditions (e.g., when the fluid 190 is absent).

The "sticky" Wenzel state of the sensor 300 created by the binding of the target analytes of interest in the fluid 190 to the binding material 130 (e.g., the analyte receptor) prevents the fluid 190 from rolling out of the (e.g., cylindrical or substantially cylindrical) air gaps 350 of the sensor 300 when the sensor 300 is tilted and/or flipped (e.g., the fluid 190 remains trapped within the air gaps/voids 350). Accordingly, the sensor 300 maintains the different color ("Color1") and does not return to its original color ("Color2") even when the sensor 300 is tilted and/or flipped, thereby providing indicia of the presence of the target analytes of interest in the fluid 190.

In some implementations, the surficial walls defining each of the (e.g., cylindrical or substantially cylindrical) air gaps/voids 350 in the base substrate 355 may be coated with a hydrophobic material. As previously mentioned, the surficial walls defining all or a select number of the (e.g., cylindrical or substantially cylindrical) air gaps/voids 350 in the base substrate 355 may also be coated with one or more thin layers of binding material 130.

The binding material can comprise or define a binding agent that binds an analyte of interest. Exemplary binding materials may include, but are not limited to a MIP material, aptamer, slow off-rate modified aptamer (SOMAmer), affimer, protein (e.g., antibody), glycoprotein, peptide, nucleic acid (e.g., deoxyribonucleic acid (DNA) and ribonucleic acid (RNA)), peptide nucleic acid (PNA), oligonucleotide, coordination complex, metal organic framework (MOF) material, porous coordination polymer material, and combinations thereof. Alternatively, instead of coating the surficial walls of the (e.g., cylindrical or substantially cylindrical) air gaps/voids 350 formed in the base substrate 355 with one or more binding material layers 130, the base substrate 355 may be made entirely or substantially from a binding material (e.g., a MIP material, an aptamer, etc.) and the surficial walls defining each of the (e.g., cylindrical or substantially cylindrical) air voids 350 may be coated with a hydrophobic material. In either case, the colorimetric sensor 300 depicted in FIGS. 3A and 3B functions as earlier described.

Figures 4A, 4B, 4C, 4D:
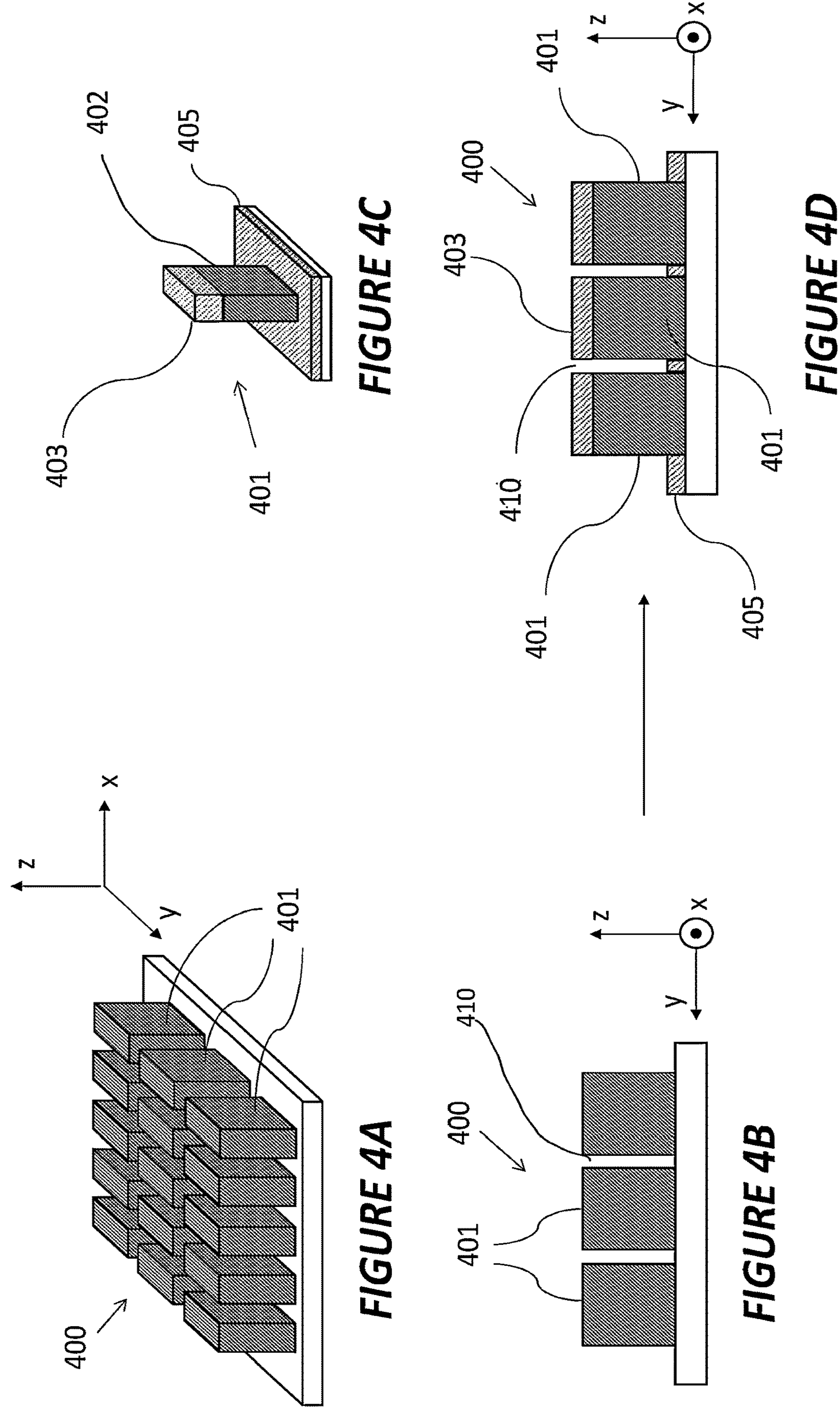
FIG. 4A shows an isometric view of a plasmonic resonance nanosensor having an array of nanopillars disposed on a back reflector, in accordance with some embodiments of the present invention.
FIG. 4B shows a side view of the nanosensor shown in FIG. 4A, in accordance with some embodiments of the present invention.
FIG. 4C shows a detail view of a plasmonic color pixel from the array of nanopillars shown in FIG. 4A, in accordance with some embodiments of the present invention.
FIG. 4D shows a side view of a plasmonic resonance nanosensor having an array of the plasmonic color pixels shown in FIG. 4C, in accordance with some embodiments of the present invention.

FIGS. 4A, 4B, and 4D depict yet another embodiment of a sensor 400 that transitions from a "non-sticky" Wenzel mode to a "sticky" Wenzel mode when an analyte of interest is present in a fluid. In particular, the sensor 400 produces plasmonic color. Plasmonic color, which results from the excitement of a surface plasmon resonance in metallic nanostructures, is another type of structural color that can produce an observable color change indicative of the presence of a target analyte of interest in a fluid. Referring to FIGS. 4A, 4B, and 4D, the colorimetric nanosensor device 400 includes an array of plasmonic color pixels 401. One such exemplary plasmonic color pixel 401 is depicted in FIG. 4C. In some applications, each plasmonic color pixel 401 may include a (e.g., metallic, rectangular-shaped) nanoblock 403 positioned on top of a (e.g., dielectric) nanopillar 402. Each nanopillar 402 may be positioned in an opening of a perforated, metallic back reflector 405. As a non-limiting example, the nanosensor 400 may be made by depositing, for example, a metallic (e.g., gold, silver, aluminum, copper, and the like) nanoblock 403 on top of each (e.g., dielectric) nanopillar 402 in an array of (e.g., dielectric) nanopillars 402, An air gap, or nanofluidic groove, 410 between adjacent (e.g., dielectric) nanopillars 402 in the array can be tuned from one (1) nm to one (1) mm; these narrow air gaps 410 can form deep interconnected nanofluidic grooves 410 as sensing channels. The surfaces of each nanopillar 402, each metallic nanoblock 403, and the metallic back reflector 405 may have additional structure with lower rank of dimensions to form a hierarchical structure as described above. Optionally, each plasmonic color pixel 401 may also include a hydrophobic coating and/or a binding material 130. For the purpose of illustration rather than limitation, exemplary binding materials 130 include aptamers, antibodies, molecularly imprinted polymers, coordination complex, and/or combinations thereof.

As will be understood by one of ordinary skill in the art, the sensor 400 operates in a similar fashion as shown in and described in connection with FIGS. 1A-1D to detect a fluid containing an analyte of interest. One slight variation is that the sensor 400 produces a plasmonic color. In particular, the change in refractive index that occurs in the sensor 400 when a fluid infiltrates the air gaps 410 of the sensor 400 can affect the dipole interaction between the metallic nanoblocks 403 positioned on the top of the nanopillars 402 and the metallic back reflector 405. This dipole interaction determines the scattered hybridized plasmon resonance, i.e., the color, exhibited by the sensor 400.

Figure 5:
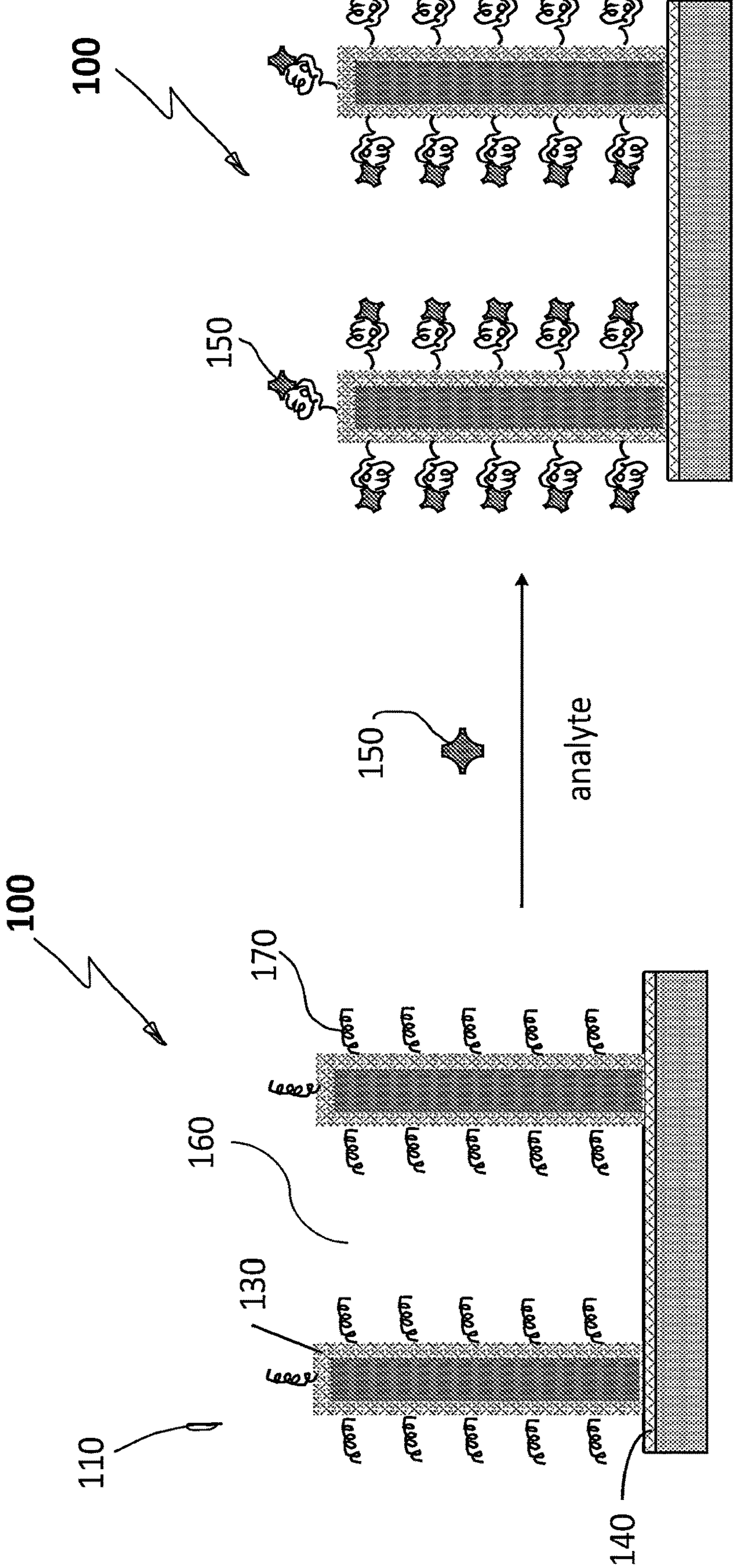
FIG. 5 shows a schematic of an exemplary sensor coated with an aptamer binding material, in accordance with some embodiments of the present invention.

As shown in FIG. 5, in some embodiments the binding material may be an aptamer 170 and the aptamer 170 may be immobilized on the surface of the transducer 110 via different conjugation approaches, including but not limited to carbodiimide crosslinking chemistry, click chemistry, glutaraldehyde crosslinking chemistry, fluorous affinity, and the like. When a fluid 180 that does not contain the target analyte of interest contacts the surface of the sensing device 100, it may penetrate the air gaps 160 of the transducer 110, but can roll off of the sensor 100 when the sensor 100 is tilted or flipped. When a fluid 190 that contains the target analyte of interest contacts the surface of the sensing device 100, it may penetrate all the air gaps 160 in the transducer 110 and the target analytes of interest 150 may bind with the aptamer 170. This induces a change in surface energy that prevents the fluid 190 from rolling off the sensor 100 when the sensor 100 is tilted or flipped.

Methods of Manufacturing the Wetting Mode-Based Colorimetric Sensors

Figure 6:
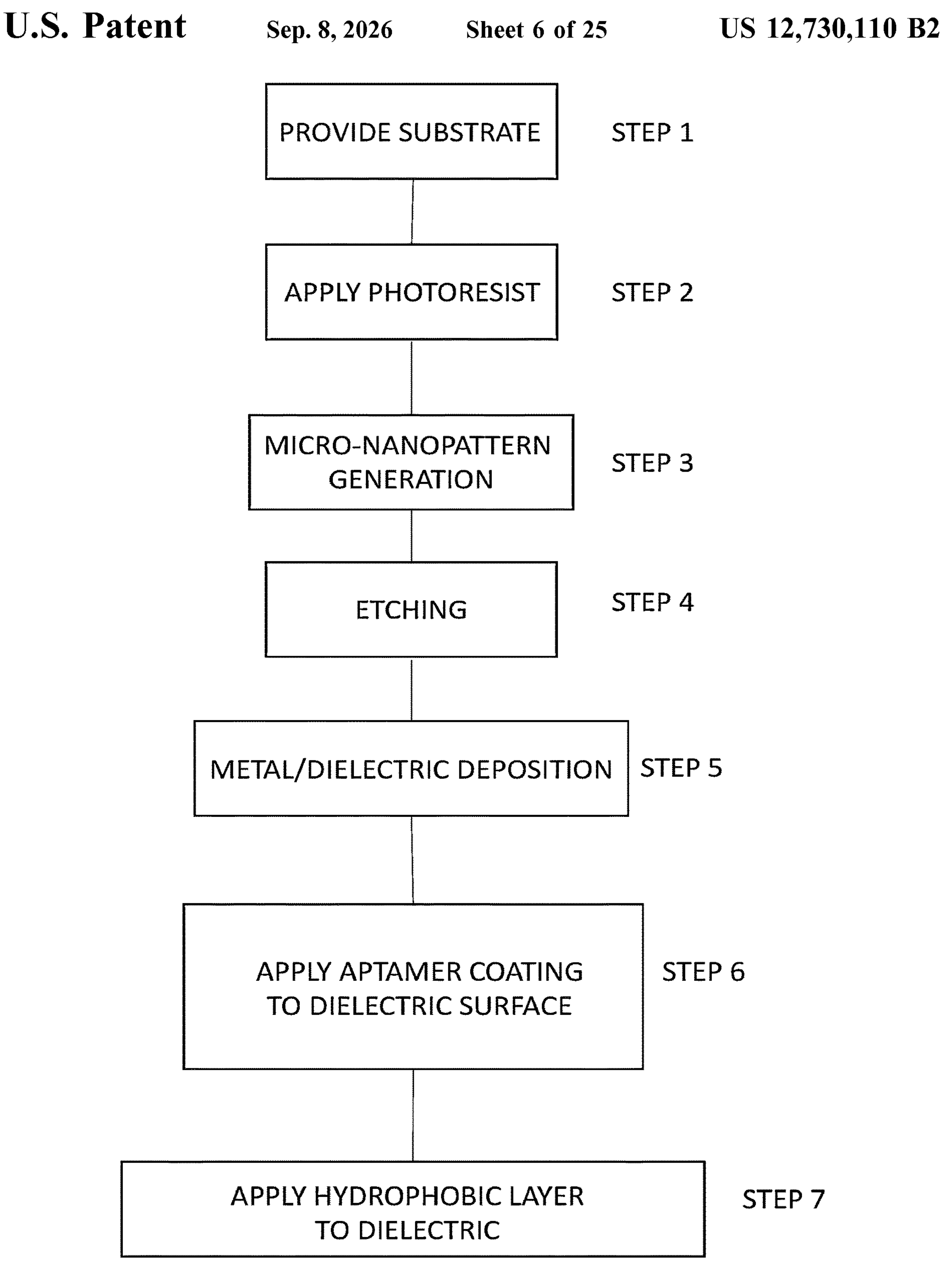
FIG. 6 shows a flow chart of an illustrative method for producing a colorimetric wetting-based sensor, in accordance with some embodiments of the present invention.

Having described a number of embodiments of sensing devices for detecting a target analyte of interest in a fluid (e.g., a liquid), exemplary methods of producing wetting-based colorimetric sensing devices will now be described. In some embodiments, with reference to FIG. 6, after providing a base substrate (STEP 1) and applying a photoresist layer (e.g., PMMA, SU8, and so forth) with a thickness between about 0.1 micrometer and about 10 micrometers to the substrate (STEP 2), a nanopattern with predetermined geometry may be generated and transferred to the photoresist layer, for example, via photolithography, electron-beam lithography (EBL), and the like (STEP 3).

Once the nanopattern has been added to the substrate, the nanopattern may be etched (STEP 4). For example, microstructures and/or nanostructures 120, 402; base substrates 355; or the like may be formed after etching part of the photoresist layer or etching into the base substrate (STEP 4). In a next step, a thin layer (e.g., of about 0.1 nm to several hundred nanometers) of metal (e.g., platinum, gold, silver, aluminium, copper, tungsten, and the like, and combinations thereof) or a dielectric material (e.g., silicon dioxide, titanium dioxide, hafnium oxide, and the like, and combinations thereof) may be applied (STEP 5) on the top surfaces of the microstructures and/or nanostructures 120, 402, as well as on the bottom surface of each microfluidic groove 160 or the like (e.g. 350, 410). Exemplary methods of applying a metal or dielectric material may include, for the purposes of illustration rather than limitation, metal deposition, chemical vapor deposition (CVD), sputtering, three-dimensional nanoprinting, plasma-enhanced chemical vapor deposition (PECVD), physical vapor deposition (PVD), electroless plating, and so forth.

In a next step, a binding material layer 130 may be applied to the metal or dielectric surface (STEP 6). In some implementations the binding material layer 130 may include aptamers, MIPs, antibodies, a combination thereof, and the like. Optionally, a hydrophobic coating may be applied to the surficial walls or part of the surficial walls of the transducer 110 (STEP 7). Alternatively, the hydrophobic coating may be applied to the surficial walls or part of the surficial walls of the transducer 110 before applying the binding materials 130.

Figure 7:
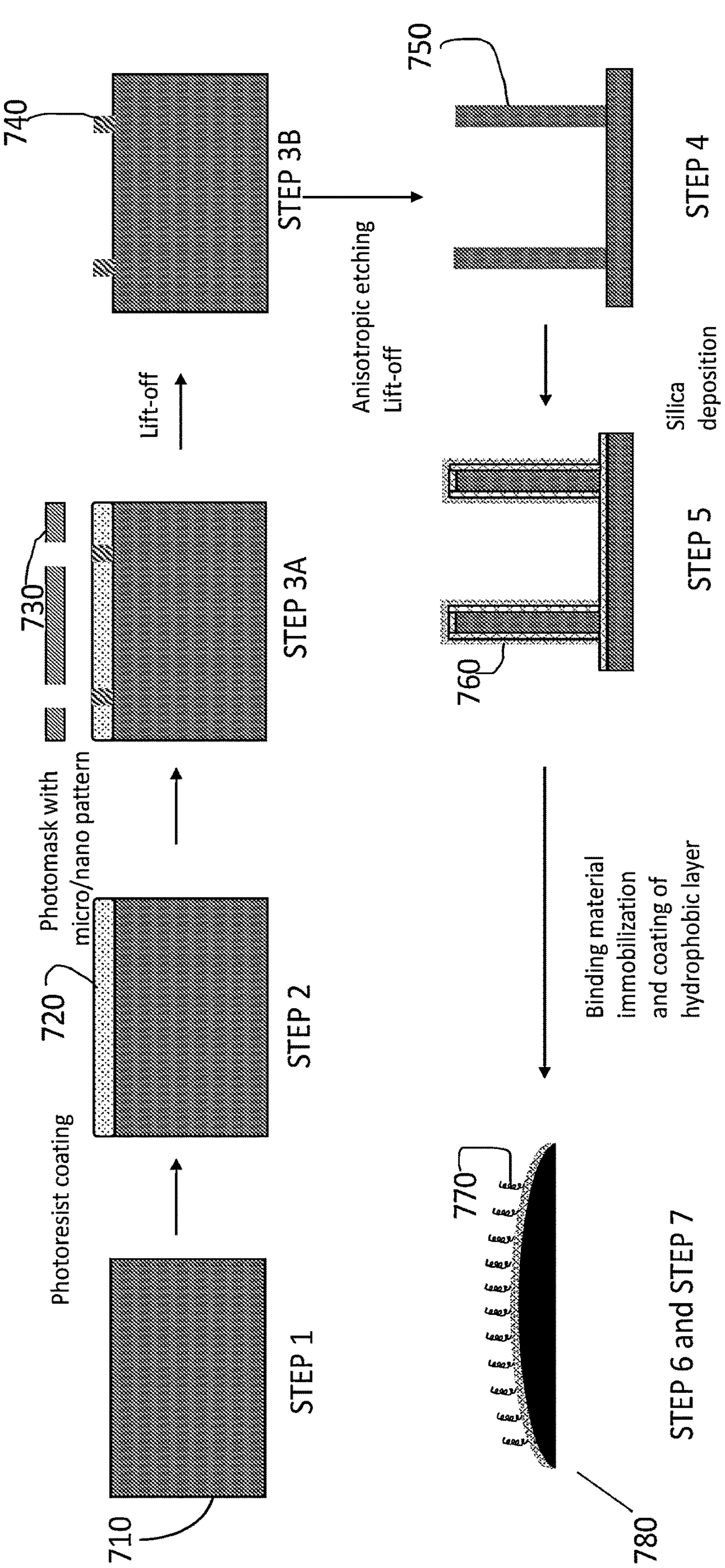
FIG. 7 shows a schematic of an exemplary method for producing a silicon-based colorimetric sensor coated with binding material and a hydrophobic layer, in accordance with some embodiments of the present invention.

Referring to FIG. 7, a first exemplary method of producing a silicon-based colorimetric sensor is shown. In some applications, in a first step, the base substrate 710 (e.g., silicon or the like) is provided (STEP 1). Subsequently, a desired thickness of a photoresist layer 720 may be applied (e.g., via spin-coating) on the surface of the silicon substrate 710 (STEP 2). A photomask 730 having a predetermined pattern (e.g., a micro-pattern, a nano-pattern, and the like) may be used to transfer the designed pattern 740 onto a negative tone photoresist (e.g., a negative tone PMMA, SU8 photoresist, and the like) (STEP 3A, 3B). Design parameters may include, for the purpose of illustration rather than limitation: the shape of the microstructures and/or nanostructures 120, 402; the size (e.g., diameter) of the microstructures and/or nanostructures 120, 402; the periodicity between the microstructures and/or nanostructures 120, 402; and so forth.

Isotropic etching may be applied to the patterned surface (STEP 4) to remove the portions of the base substrate 710 that are not disposed immediately beneath the design pattern 740. Exemplary methods of etching include, for the purpose of illustration rather than limitation: electrochemical etching, wet-etching, dry-etching, and laser-induced etching. For example, in some variations, deep reactive ion etching, which can involve either a wet- or a dry-etching process, may be employed to form the microstructures and/or nanostructures 750 in the base substrate 710 using the patterned photoresist as an etching mask. In some variations, a Bosch process may be used to achieve high aspect ratio microstructures and/or nanostructures 750 with roughness on the sidewalls of microstructures and/or nanostructures 750. As another non-limiting example, a high-energy laser may be employed in a laser-induced etching process to form precise microstructures and/or nanostructures 750 in the base substrate 710 by etching away the material in the base substrate 710.

A silica, thin film 760 having a desired grain size (e.g., grains having a nanometre scale) may then be deposited onto the surface of the microstructures (and/or nanostructures) 750 (e.g., via a PECVD process) (STEP 5). In some variations, silica nanoparticles may also be deposited to the surface of microstructures and/or nanostructures 750. The silica nanoparticles may be crosslinked with each other and covalently grafted to the microstructure surface 750 to enable a micro-nano hierarchical structure. Furthermore, the silica nanoparticles may be coated with an additional third-rank of molecular layers (e.g., a polymer layer with controlled thickness) to produce a micro-nano-angstrom hierarchical structure. The thickness of the silica thin film 760 may be in the range of about 0.1 nm to several hundred of micrometers depending on the dimensions of the microstructures and/or nanostructures 750.

A binding material 770 (e.g., aptamers, MIPs, antibodies, and the like) and a hydrophobic layer 780 (e.g., a fluorinated silane molecule, and the like) may then be applied to the surficial walls of the hierarchical structure. The order of the binding materials 770 and the hydrophobic layer 780 may be swapped depending on the immobilization method to be used. The hydrophobic coating 780 may be applied in a variety of manners. For example, where the hydrophobic coating 780 includes silane molecules, the hydrophobic coating 780 may be applied via vapor phase deposition. As additional examples, where the hydrophobic coating 780 includes dielectric materials (e.g., titanium dioxide, silicon dioxide, hafnium oxide, and the like), the hydrophobic coating 780 may be applied via, for example: atomic layer deposition (ALD), plasma-enhanced chemical vapor deposition (PECVD), or physical vapor deposition (PVD). As yet another example, where the hydrophobic coating 780 includes metallic materials (e.g., gold, silver, aluminum, copper, and the like), the hydrophobic coating 780 may be applied via, e.g., an electron-beam evaporation process. In an exemplary implementation where the binding material 770 itself is hydrophobic, the additional hydrophobic coating 780 may be unnecessary.

Figure 8:
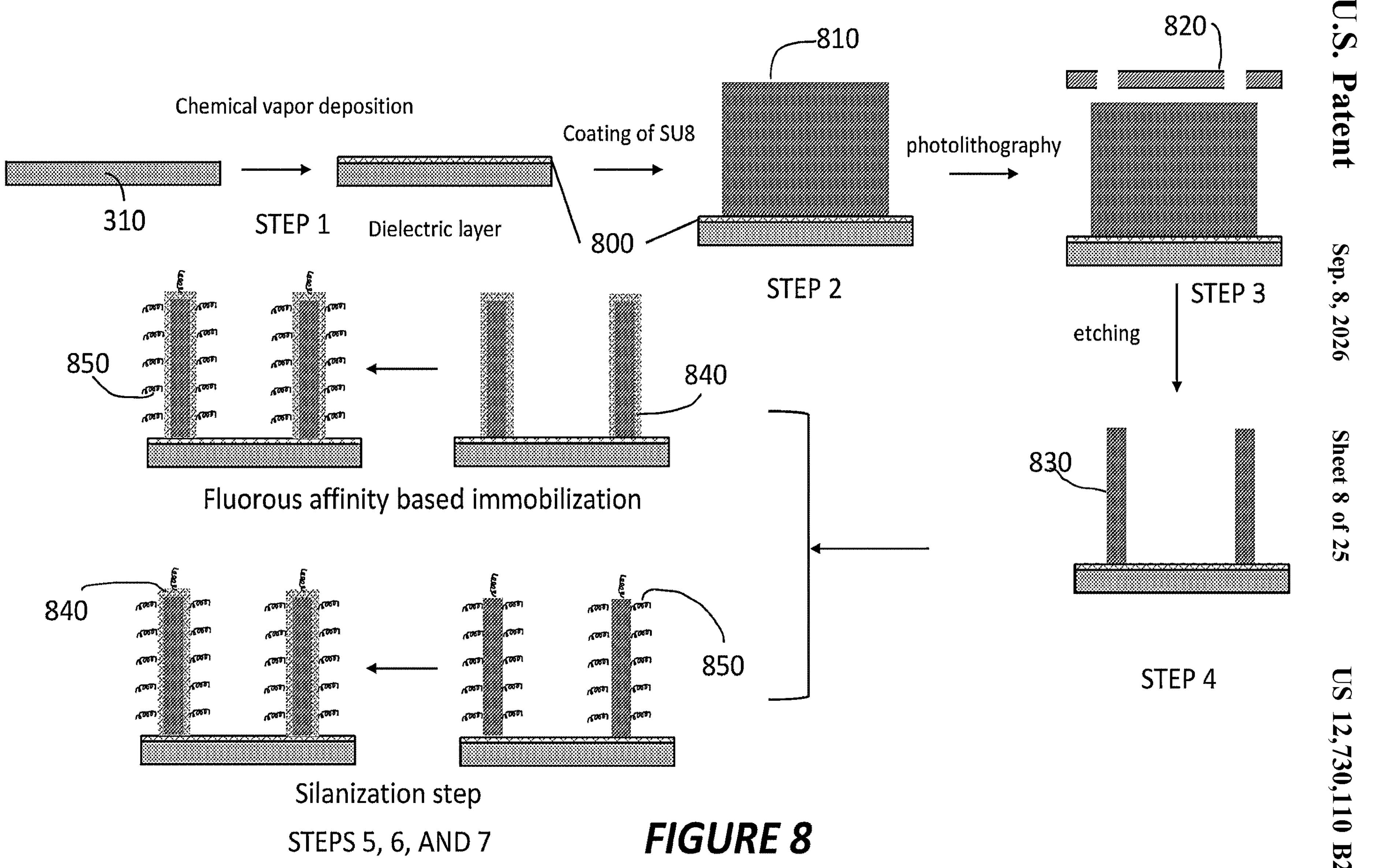
FIG. 8 shows a schematic of a method for producing a SU8-based colorimetric sensor coated with binding material and a hydrophobic layer, in accordance with some embodiments of the present invention.

Referring to FIG. 8, a second exemplary method of producing a SU8-based colorimetric sensor is shown. In a first step, a substrate 310 onto which a relatively thin layer of (e.g., dielectric, metallic, and the like) material (e.g., an indicator layer 800) has been applied (e.g., via chemical vapor deposition) may be provided (STEP 1). The thin layer of indicator 800 may include, but is not limited to: a thin layer of silicon dioxide 800 (e.g., from 0.1 nm to several hundred micrometers) deposited on a silicon substrate 310, a thin layer of germanium 800 (e.g., from 0.1 nm to several hundred micrometers) deposited on a gold substrate 310, and the like. Subsequently, a (e.g., SU8) photoresist layer 810 may be applied to the top of the thin layer of indicator 800 (STEP 2). In some variations, the thickness of the (e.g., SU8) photoresist layer 810 may range between about 0.1 micrometers to about 10 micrometers.

A photomask 820 having a predetermined pattern (e.g., a micro-pattern, a nano-pattern, and the like) may be applied and used to transfer the desired pattern onto the SU8 photoresist 810 (STEP 3). Design parameters may include, for the purpose of illustration rather than limitation: the size (e.g., diameter or other dimension) of the resulting microstructures and/or nanostructures 830, the shape of the resulting microstructures and/or nanostructures 830, the periodicity between the resulting microstructures and/or nanostructures 830, and so forth.

Etching (e.g., isotropic etching) may be applied to the patterned surface (STEP 4) to remove the portions of the SU8 photoresist 810 that are not disposed immediately beneath the design pattern 820. Exemplary methods of etching include, for the purpose of illustration and not limitation: electrochemical etching, wet-etching, dry-etching, and laser-induced etching. For example, deep reactive ion etching, which can involve either a wet- or a dry-etching process, may be employed to form the microstructures and/or nanostructures 830 using the patterned photoresist 820 as an etching mask. In some variations, a Bosch process may be used to achieve high aspect ratio microstructures and/or nanostructures 830 with roughness on the sidewalls of the microstructures and/or nanostructures 830.

After SU8 microstructures and/or nanostructures 830 are produced, deposition may be performed to coat the surficial walls of SU8 microstructures and/or nanostructures 830 with a thin layer 840 (e.g., from 0.1 nm to several hundred micrometers) of silicon dioxide or other materials (STEP 5). In addition to silicon dioxide, the thin layer 840 may include, for the purpose of illustration rather than limitation: dielectric materials, oxides, semiconductors, metals, combinations thereof, and the like. In some variations, the thin layer 840 may be a continuous film (e.g., a smooth film with surface roughness less than 0.1 nm); while, in other variations, the thin layer 840 may include isolated island structures (e.g., island nanostructures).

In a next step, a binding material 850 (e.g., aptamers, MIPs, antibodies, and the like) (STEP 6) and/or an immobilization and hydrophobic layer (STEP 7) may be coated on the SU8 microstructures and/or nanostructures 830 and/or on the thin layer 840. For example, in one variation, an immobilization method may involve a fluorous affinity-based interaction between a fluorous binding material 850 and a fluorous anchor molecule disposed on the surface of the microstructures and/or nanostructures 830. In another example, a fluorinated silane 840 may be applied after immobilization of binding materials 850 onto the surface of the microstructures and/or nanostructures 830.

Referring to the transducer 300 depicted in FIG. 3A (including base substrate 355 and air gaps/voids 350), a method of manufacturing a hole-based or air gap/void-based colorimetric sensor 300 will now be described. In some implementations, the base substrate 355 may be, for example, synthesized from a homogenous liquid precursor of a polymer material, which may be an organic, inorganic, or hybrid polymer material, under suitable reaction conditions. As a non-limiting example, where the base substrate is manufactured from or includes silica, the base substrate 355 may be formed from its sol-gel precursor tetraethyl orthosilicate (TEOS) under suitable conditions. As another non-limiting example, where the base substrate 355 is manufactured from or includes titanium dioxide, the base substrate may be formed from its precursors tetraiso-propylorthotitanate (e.g., $Ti(OC_3H_7)_4$ or "TIPT") and/or titanium tetrachloride ($TiCl_4$) under suitable conditions. The base substrate 355 may also include metal nanoparticles fully embedded in the base substrate 355 or exposed (or partially exposed) to air gaps/voids 350.

In greater detail, in accordance with a method of manufacturing the colorimetric sensor 300 of FIG. 3A, a liquid precursor of the appropriate organic, inorganic, or hybrid (e.g., TEOS, (3-aminopropyl)triethoxysilane (APTES), or suitable silane molecules) polymer material may be mixed homogeneously with target analyte molecules of interest that act as templates for molecularly imprinting purposes, e.g., to create cavities for recognition of the target analyte molecule. In some embodiments, this mixed liquid precursor of the organic, inorganic, or hybrid polymer material may be mixed with and include porogens (e.g., nanocylinders, microcylinders, etc.), which may be fugitive materials, for creating the air gaps/voids 350. The shape of the air gaps/voids 350 may be cylindrical or whatever is the shape of the porogen. The mixed liquid precursor also can include metal (e.g., gold, silver, platinum, and the like) nanoparticles via a sol-gel process. The mixed liquid precursor then may be solidified under suitable reaction conditions, such as under moderate temperature (e.g., a temperature from room temperature to 300° C.) to lock in the porogens in periodic, aperiodic, and/or random positions (e.g., such that neighboring porogens are spaced apart by a distance between 0.1 nanometer and 1000 micrometers or by a distance corresponding to a wavelength range of visible light).

Solidification methods may include, but are not limited to, thermal treatment, photo-induced solidification, radiation-induced solidification, and chemical reaction-induced solidification. In some embodiments, the target analyte molecules of interest that act as cavity templates may then be removed to form the molecularly-imprinted cavities of the MIP. Analyte molecule templates may be removed using, for example, a Soxhlet extraction process, a sonication process, a washing process with suitable solvent (e.g., methanol/acetic acid or other solvents and combinations thereof). The porogens that form the cylindrical or other shaped air gaps/voids 350, such as colloidal porogens (e.g., cylindrical latex nanoparticles) may be removed using a thermal process (e.g., sintering above 500° C.) or by dissolution using a suitable solvent or solvent system. At least some of the resulting cylindrical or other shaped air gaps/voids 350 may be interconnected or, alternatively, the resulting cylindrical or other shaped air gaps/voids 350 may be isolated from one another. Moreover, as described, the porogens used to form the air gaps/voids 350 may have a shape other than cylindrical (e.g., spherical or another shape).

In some variations, for example, when the base substrate is a MIP, once the base substrate 355 having air gaps/voids 350 has been synthesized, an optional deposition step may be performed to coat the surficial walls of the air gaps/voids 350 and the base substrate 355 with a thin layer of silicon dioxide (e.g., from 0.1 nm to the largest dimension of the air gaps/voids 350), or other materials including but are not limited to dielectric materials, oxides, semiconductors, metals, combinations thereof, and the like. The thin layer may be a continuous film (e.g., a smooth film with surface roughness less than 0.1 nm), or the thin layer may comprise isolated island structures (e.g., island nanostructures) as shown in FIG. 3B. Exemplary deposition methods include, but are not limited to, atomic layer deposition (ALD), plasma-enhanced chemical vapor deposition (PECVD), or physical vapor deposition (PVD).

Furthermore, a hydrophobic coating may be applied to the surficial walls defining each of the air gaps/voids 350 in a variety of manners. For example, where the hydrophobic coating includes silane molecules, the hydrophobic coating may be applied via vapor phase deposition. Alternatively, the hydrophobic coating may be applied via atomic layer deposition (ALD), plasma-enhanced chemical vapor deposition (PECVD), or physical vapor deposition (PVD). As yet another example, where the hydrophobic coating includes metallic materials (e.g., gold, silver, aluminum, copper, etc.), the hydrophobic coating may be applied via an electron-beam evaporation process.

Figure 9:
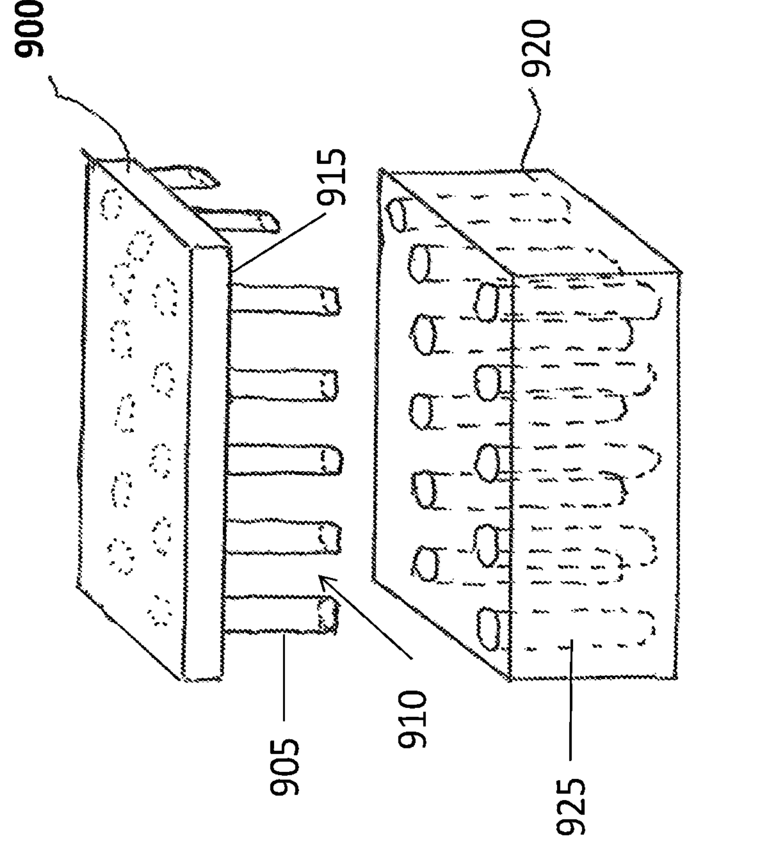
FIG. 9 shows a mold for forming air gaps in a base substrate, in accordance with some embodiments of the present invention.

Referring now to FIG. 9, as an alternative to an etching process, in another exemplary method of manufacture, colorimetric sensors may be manufactured using a pillar-like mold 900. The pillar-shaped mold 900 is used as an example for the purpose of illustration rather than limitation. Those of ordinary skill in the art can appreciate that other types of molds (e.g., a hole-like mold) may be used for imprinting to produce a pillar-based structure. The pillar-like mold 900 may be made of, for example, silicone or some other suitable mold material such as silicon, polyethylene terephthalate (PET), a UV-curable resin, and the like. In some implementations, the mold 900 is structured and arranged to include, on a bottom portion 915 thereof, solid portions 905 with openings 910 therebetween. The solid portions 905 are structured and arranged to provide a negative or mirrored image of a desired array of air gaps/voids 925 in a base substrate 920. As will be appreciated by those of ordinary skill in the art, although FIG. 9 shows a method in which the solid portions 905 are formed on the bottom portion 915 of the mold 900 and the bottom portion 915 is pressed into a top surface of the base substrate 920, the solid portions 905 may, instead, be formed on a top portion of the mold 900 and the top portion pressed into the base substrate 920.

The solid portions 905 of the mold 900 may be configured to provide, in the base substrate 920, a resulting array of air gaps/voids 925 that each has a desired size, shape, depth, periodicity, and so forth. Although the shape and size of each solid portion 905 may be the same or substantially the same as one another, those of ordinary skill in the art can appreciate and understand that the solid portions 905 may instead be sized and shaped differently from one another so as to provide air gaps/voids 925 of differing sizes, shapes, and depths, as well as of differing periodicity.

Figure 10:
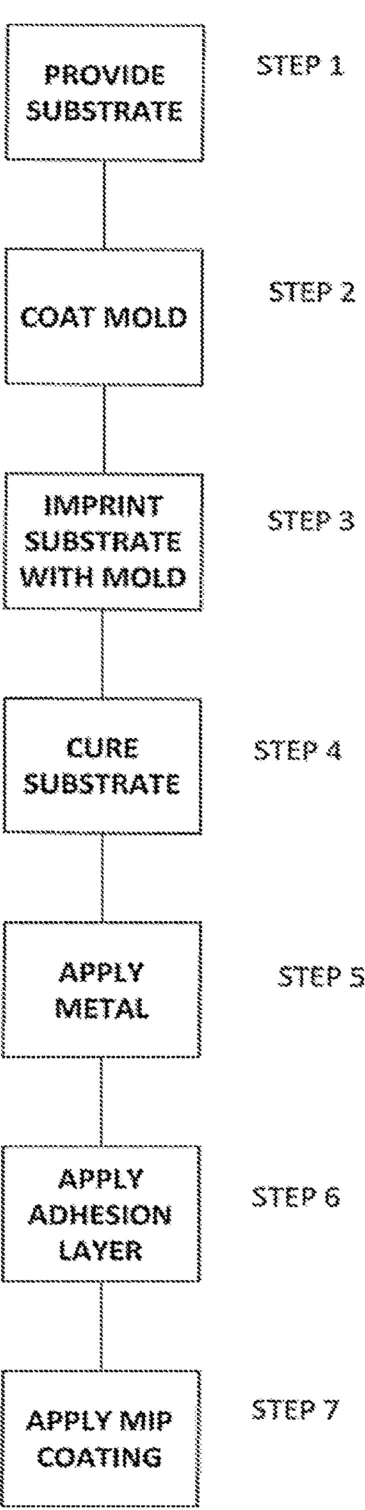
FIG. 10 shows a flow chart of an illustrative method for manufacturing a colorimetric sensor using an imprinting process, in accordance with some embodiments of the present invention.

In accordance with an exemplary method, and with reference now also to FIG. 10, after providing the base substrate 920 and mold 900 (STEP 1), the surfaces of the solid portions 905 of the mold 900 may be coated (STEP 2) with a very thin layer of a releasing agent (e.g., fluorocarbon, fluorosilane, polybenzoxazine, combinations thereof, and the like) to facilitate removal of the mold 900 from the resulting array of air gaps/voids 925. The very thin layer or coating of the releasing agent can be a self-assembled monolayer (SAM) or multiple layers with a thickness from less than about one (1) Angstrom to about 10 nm. The base substrate 920 may then be imprinted with the mold 900 (STEP 3).

Following the imprinting of the air gaps/voids 925 in the base substrate 920 and depending on the material used to manufacture the base substrate 920, the imprinted substrate 920 may be cured (STEP 4), for example, via photo- (e.g., using ultraviolet (UV) light) or thermal-initiated polymerization.

In a next step, depending on the structural color generation mechanism, a thin layer (e.g., of about 0.1 nm to several hundred micrometers) of dielectric (e.g., silicon dioxide, titanium dioxide, hafnium oxide, and the like, and combinations thereof) or metal (e.g., platinum, gold, silver, aluminium, copper, tungsten, combinations thereof, and the like) may be applied (STEP 5) on the top surface of the base substrate 920, as well as on the bottom surface of each air gap/void 925. Exemplary methods of applying a dielectric or metal may include, for the purpose of illustration rather than limitation: metal deposition, chemical vapor deposition (CVD), sputtering, three-dimensional nanoprinting, plasma-enhanced chemical vapor deposition (PECVD), physical vapor deposition (PVD), electroless plating, and so forth. In some variations, the deposition may be on all or part of the surficial walls defining the air gaps/voids 925. Deposition on the top surface of the base substrate 920 may form a continuous metal film atop the substrate 920 and about the array of air gaps/voids 925. In the alternative, an annular metal nanodisk concentric with or substantially concentric with the opening of each air gap/void 925 may be formed on the top surface of the substrate 920 about each air gap/void 925 opening.

A hydrophobic coating may then be applied to the surficial walls defining each of the air gaps/voids 925 and (if the base substrate 920 is not itself a binding material) a binding material layer (e.g., a MIP material) may be applied as a coating to the surficial walls defining all or a select number of the air gaps/voids 925. Both the hydrophobic coating and the binding material coating may be applied to the applicable surfaces as explained above. As another example, in a case where the air gaps/voids 925 are formed in a dielectric material to be coated with a binding material (e.g., a MIP material, an aptamer), a thin (e.g., 0.1 nm to 100 nm thick) adhesion layer of silica may be applied to the surficial walls of the air gaps/voids 925 (STEP 6). Exemplary methods of applying an adhesion layer to the surficial walls of the air gaps/voids 925 may include, for the purpose of illustration rather than limitation: atomic layer deposition (ALD), chemical vapor deposition (CVD), physical vapor deposition (PVD), electron beam evaporation, or sputtering. Subsequently, a soluble and processible MIP or aptamer may be applied to the silica surface as a thin (e.g., 0.1 nm to 100 nm thick) coating (STEP 7). Exemplary methods of applying soluble and processible MIP or aptamer to the silica surface may include, for the purpose of illustration rather than limitation: spin-coating, dip-coating, covalently binding, and the like.

Exemplary Binding Materials and Methods of Attachment to the Sensors

In some applications, the binding material 130 may be an aptamer. Aptamers are single stranded oligonucleotide molecules that bind a specific target molecule. Aptamers with specificity for a target molecule are identified by screening oligonucleotide libraries using a process called SELEX (systematic evolution of ligands by exponential enrichment) (see, Tuerk et al., Science, (1990) 249 (4968): 505-510; Ellington et al. Nature, (1990) 346 (6287): 818-822; Robertson et al. Nature (1990) 344(6265): 467-468). The terminal functional groups of an aptamer may be modified to allow the attachment and coating of an aptamer to a colorimetric sensor surface. Although aptamers may be bound to the surface via covalent bonds, those of ordinary skill in the art can appreciate that aptamers may also be bound to the sensor surfaces via other types of chemical interaction, including but not limited to, non-covalent interactions, ionic bonds, van der Waals forces, electrostatic forces, hydrogen bonding, fluorous affinity, and Pi-Pi stacking interactions.

In some applications, the aptamer for use as described herein (e.g., as a binding material, layer, and/or coating) may generally be manufactured by oligonucleotide synthesis using phosphoramidite chemistry, which was developed in the 1980s and later enhanced with solid-phase supports and automation. (see, Oligonucleotide Synthesis: Methods and Applications. Edited by Piet Herdewijn, Humana Press: Totowa, NJ 2005). To obtain the desired aptamer, the building blocks are sequentially inserted into the growing oligonucleotide chain in the order of the aptamer sequence from the 3' to 5' direction. Typical number of nucleotides may be selected between 1 nucleotide and 200 nucleotides, between 10 nucleotides and 100 nucleotides, or between 30 and 80 nucleotides. Typical building blocks include, for the purpose of illustration and not limitation, nucleoside phosphoramidites, non-nucleoside phosphoramidites, and the like. In some implementations, the aptamer may be chemically modified at either its 5' or 3' end with specific functional groups that facilitate the crosslinking to the surface of the transducer 110 (e.g., amine modification). FIG. 11 illustrates an exemplary scheme for conjugating an aminated aptamer to a surface via glutaraldehyde crosslinking in a 4-step process. STEP 1 may include an activation process to produce a hydroxyl-rich surface. The activation process may include, but is not limited to, an oxygen plasma treatment of the surface, a piranha solution mediated surface treatment, and the like. STEP 2 may include an amination process in which (3-Aminopropyl)triethoxysilane (APTES) is reacted with the hydroxyl-rich surface from STEP 1. This amination process may occur in either the solution phase or gaseous phase. For example, the amination may proceed at room temperature in a 2% APTES solution in toluene for one hour, or in APTES vapor phase within a sealed reactor at 150° C. Subsequently in STEP 3, the aminated surface may be reacted with one of the two carbonyl functional groups of a glutaraldehyde crosslinker to yield a carbonyl-rich surface. Then in STEP 4 the aminated aptamer, which is made using a standard oligo modification (e.g., from Integrated DNA Technologies, Inc.), may be covalently linked to the carbonyl-rich surface of STEP 3 by reacting with the carbonyl functional groups of the glutaraldehyde crosslinker.

Figure 12:
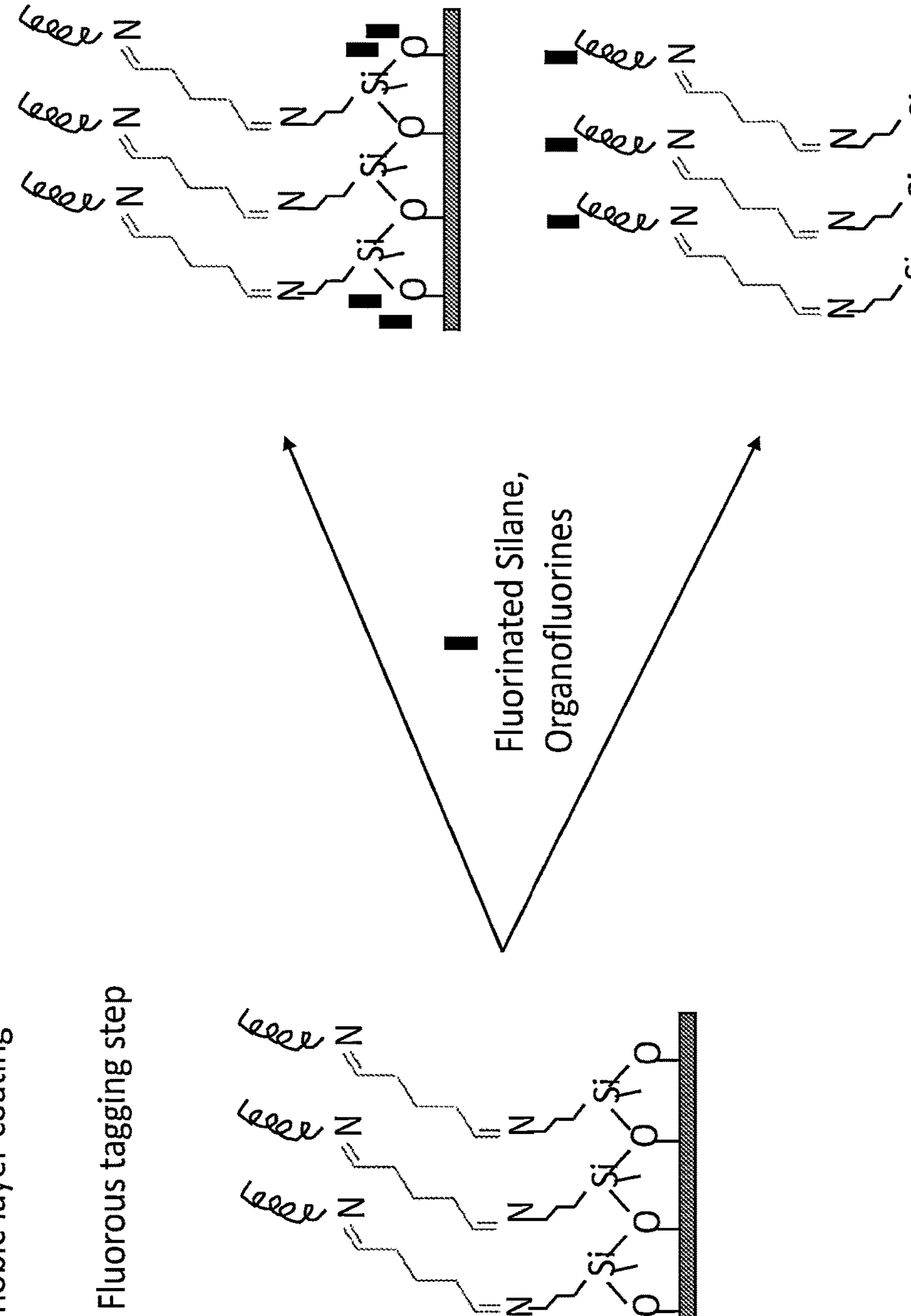
FIG. 12 shows an exemplary schematic for applying a hydrophobic layer to a sensor after the attachment of binding materials, in accordance with some embodiments of the present invention.

FIG. 12 depicts an exemplary scheme for applying a hydrophobic coating to a sensor surface after attachment of the binding material (e.g., aptamers). Compounds with long alkyl chains, fluorinated silanes (e.g., 1H,1H,2H,2H-perfluorooctyltrichlorosilane, Octadecyltrichlorosilane, and the like), organofluorine compounds, perfluorocarbons, fluoropolymers, hydrofluorocarbons, fluorocarbenes, combinations thereof, and the like may be deposited on the sensor surface via liquid or vapor phase deposition. This hydrophobic coating may be formed at different locations of the sensor as shown in FIG. 12. These locations may include the surface of the transducer, the surface of the aptamer, or a combination thereof. The hydrophobic molecular coating may be covalently grafted to the surface, physically adsorbed to the surface, a combination thereof. Those of ordinary skill in the art can appreciate that, in some embodiments, organofluorine gas (e.g., $C_4F_8$ as a non-limiting example) may be used in a plasma process to generate free radicals or fragments and deposited on the micro/nanopillar surface or covalently grafted to the aptamer, or physically deposited on the surface via other molecular interactions than covalent bonding. One of ordinary skill in the art will appreciate that other techniques may be used to coat the sensor surface with these hydrophobic materials.

Figure 13:
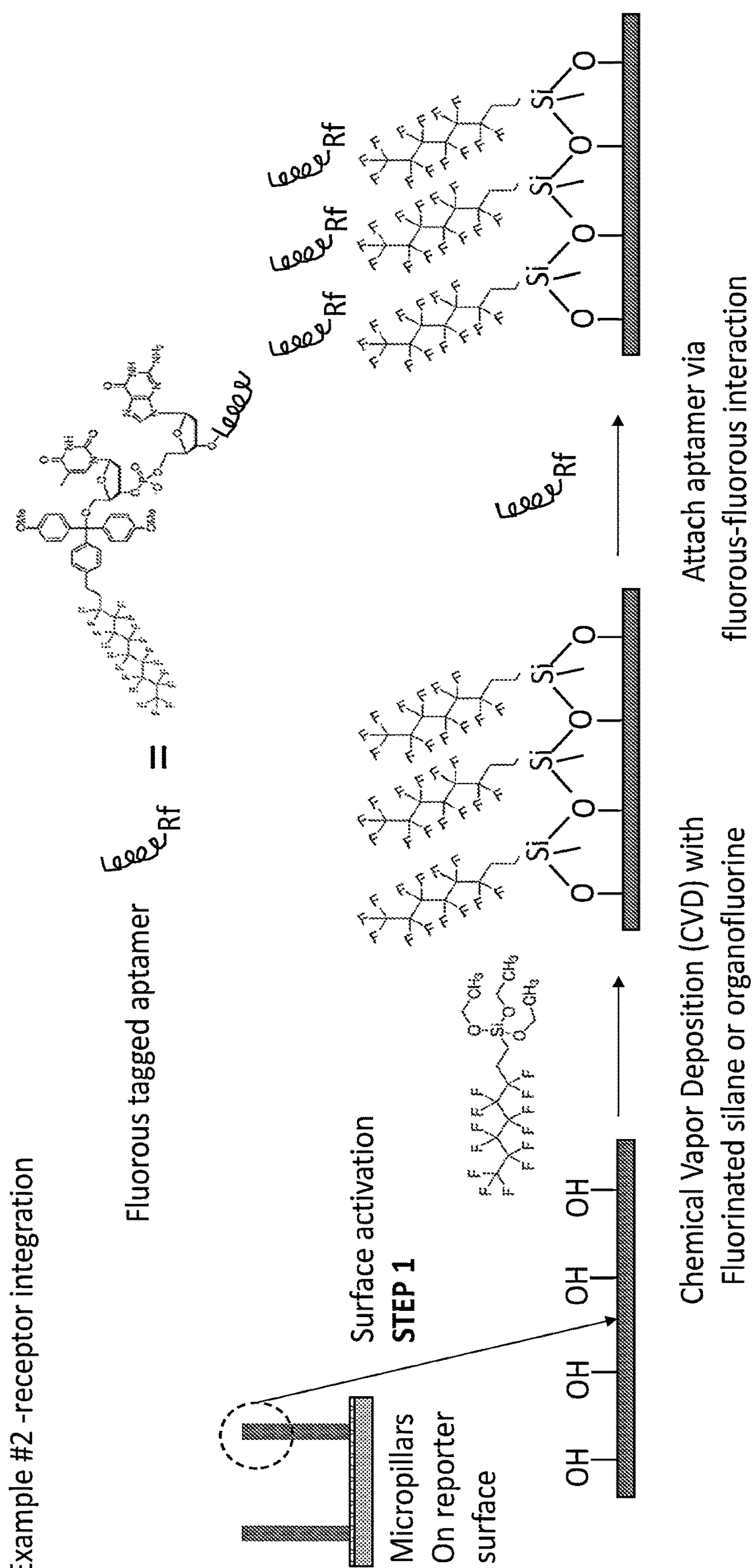
FIG. 13 shows a schematic of an exemplary method for attaching a fluorinated aptamer to a fluorinated-silane sensor surface, in accordance with some embodiments of the present invention.

In some implementations, the aptamer may be attached to the sensor surface using fluorous affinity. For example, FIG. 13 demonstrates a 3-step process to immobilize a receptor (e.g., an aptamer) to the surface. STEP 1 may include an activation process to produce a hydroxyl-rich surface. The activation process may include, but is not limited to, an oxygen plasma treatment of the surface, a piranha solution mediated surface treatment, and the like. In STEP 2, the activated transducer surface (e.g., a silicon dioxide surface) may be functionalized with fluorous molecules. For example, fluorous silane (e.g., 1H,1H,2H,2H-perfluorooctyltriethoxysilane or the like) may be covalently grafted to the activated transducer surface via a chemical vapor deposition (CVD) process. Those of ordinary skill in the art can appreciate that, in some embodiments, organofluorine gas (e.g., $C_4F_8$ as a non-limiting example) may be used in a plasma CVD process to generate free radicals or fragments and deposited on the micro/nanopillar transducer surface. In STEP 3, a fluorous tagged aptamer may be attached to the fluorinated transducer surface via fluorous-fluorous interaction. Fluorous tagged aptamers may be produced using well-known oligo modification procedures described in, for example, Pearson et al. J. Org. Chem. (2005), 70, 7114-7122; Beller et al. Chim. Acta 2005, 88, 171-179; Tripathi et al. Org. Prep. Proc. Int. 2005, 37, 257-263.

Figure 14:
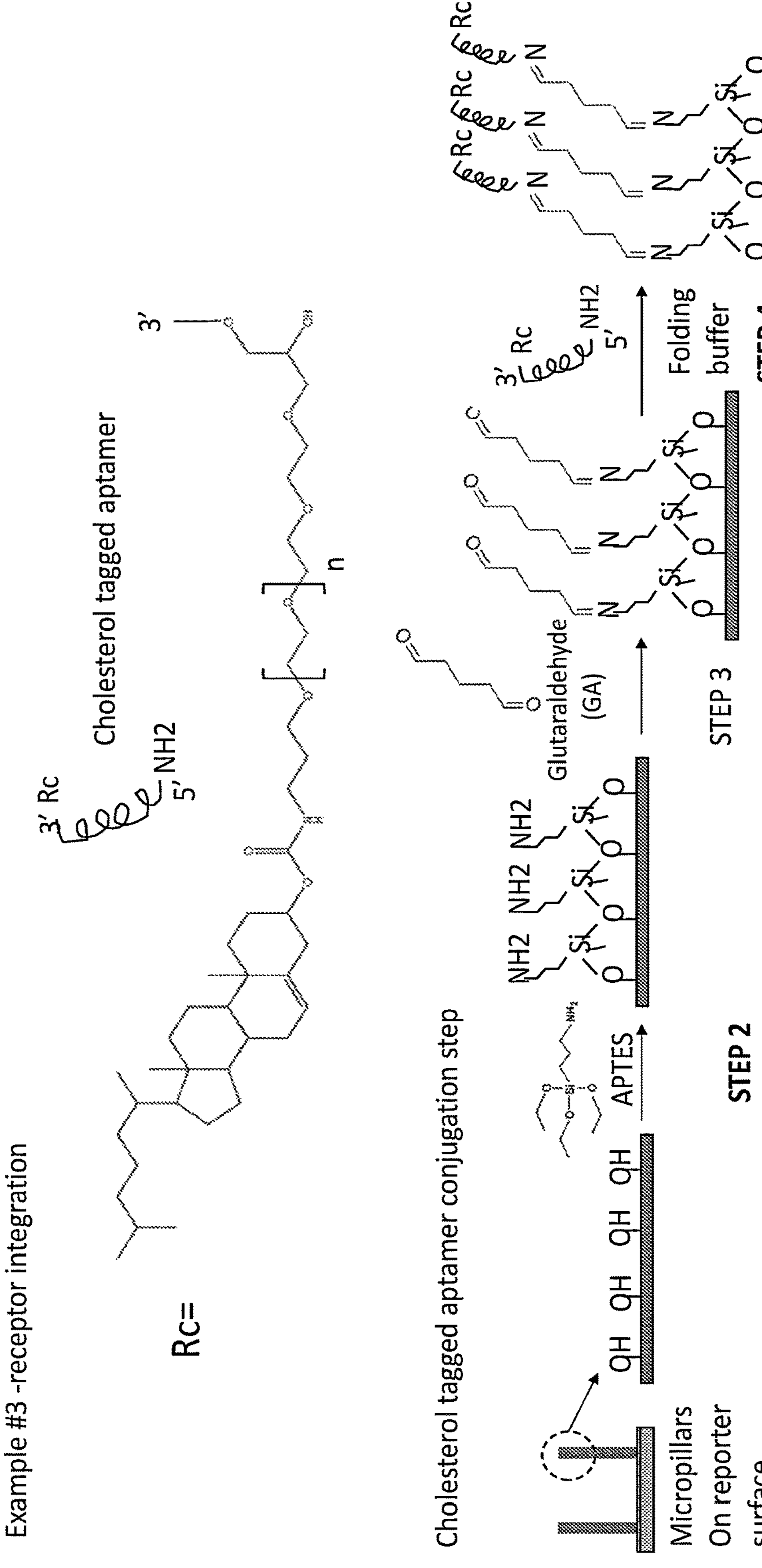
FIG. 14 shows a schematic of an exemplary method for attaching a cholesterol tagged aptamer, in accordance with some embodiments of the present invention.

In some embodiments, in order to prepare an initial hydrophobic surface, the binding material may be produced using hydrophobic components (e.g., the binding material itself is hydrophobic; a hydrophilic binding material coated with a hydrophobic layer; or a combination thereof). FIG. 14 shows how a hydrophobic lipid molecule, such as cholesterol, may be tagged to the 3' (or 5') end of an aptamer while a primary amine group may be tagged to the 5' (or 3') end of the aptamer. This tagged aptamer can be made using a standard oligo modification process (e.g., from Integrated DNA Technologies, Inc.), a hydrophilic spacer may be introduced between the aptamer and the hydrophobic cholesterol tag to fine tune the hydrophobicity to the desired level. For the purpose of illustration rather than limitation, the primary amine group is used to attach the aptamer to the sensor surface via glutaraldehyde crosslinking chemistry, as described above using a 4-step process. In some applications, a folding buffer may be used to fold the aptamer into the desired 3D structure. Exemplary folding buffers include, but are not limited to, 137 mM NaCl, 2.7 mM KCl, 6.5 mM Na2HPO4, 1.8 mM NaH2PO4, 1.47 mM MgCl2, 0.05% Tween-20, and 0.1% (w/v) bovine serum albumin (BSA).

Figure 15:
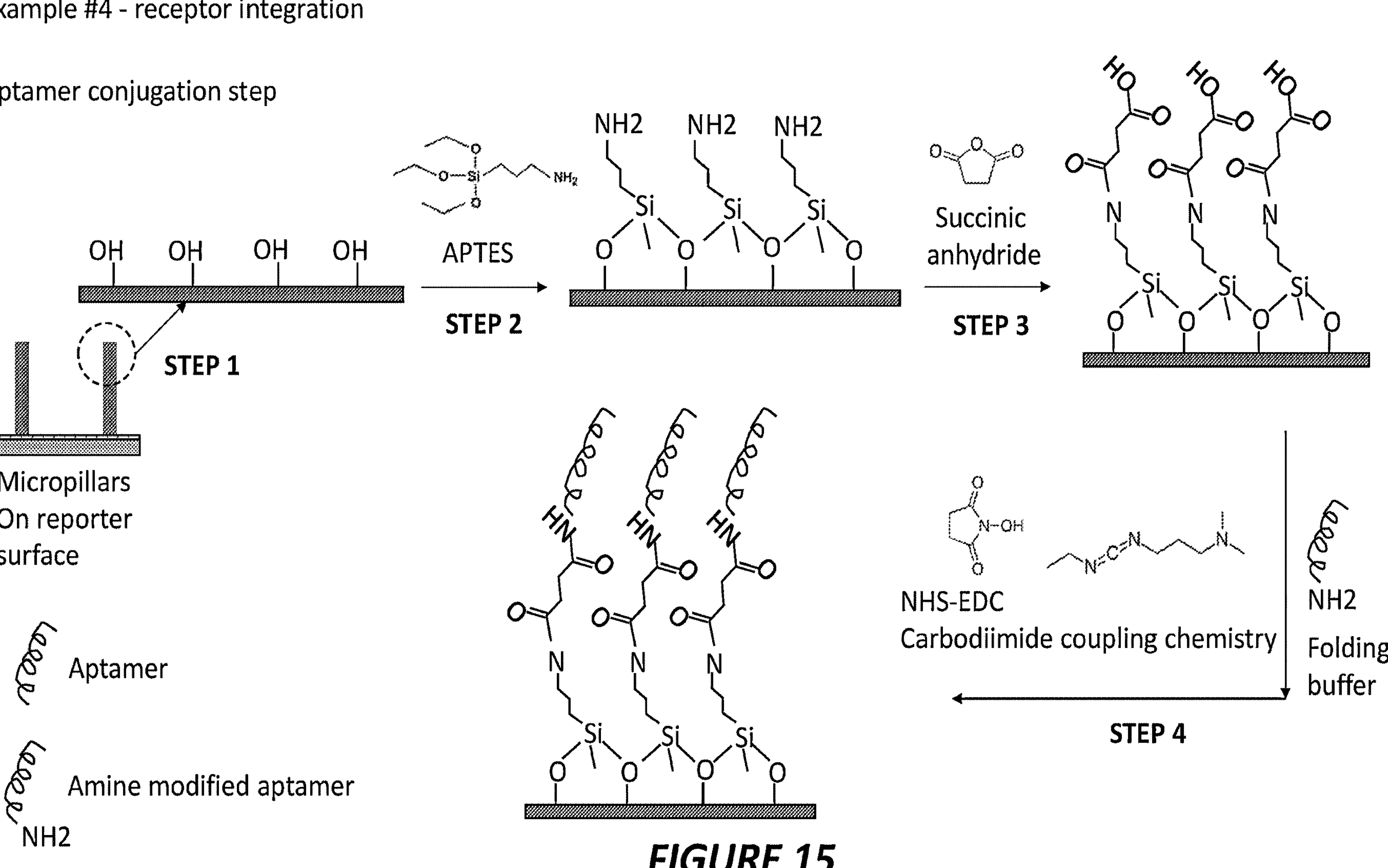
FIG. 15 shows a schematic of an exemplary method of conjugating an aptamer to a sensor surface via a carboxyl-to-amine crosslinking method, in accordance with some embodiments of the present invention.

In yet another embodiment, amine modified aptamers may be attached to the sensor surface via carbodiimide crosslinking chemistry. FIG. 15 demonstrates a four-step carboxyl-to-amine crosslinking process. STEP 1 may include an activation process to produce a hydroxyl-rich surface. The activation process may include, but is not limited to, an oxygen plasma treatment of the surface, a piranha solution mediated surface treatment, and the like. STEP 2 may include an amination process in which (3-Aminopropyl)triethoxysilane (APTES) is reacted with the hydroxyl-rich surface from STEP 1 to generate an amine-rich surface. This amination process may occur in either the solution phase or gaseous phase. For example, the amination may proceed at room temperature in a 2% APTES solution in toluene for one hour, or in APTES vapor phase within a sealed reactor at 150° C. Subsequently in STEP 3 the amine-rich surface may be converted into a carboxylic-rich surface via a ring opening amidation reaction of succinic anhydride with the primary amine groups on the sensor surface at room temperature. Finally, STEP 4 includes an EDC/NHS (1-Ethyl-3-[3-dimethylaminopropyl]carbodiimide hydrochloride/N-hydroxysuccinimide) coupling chemistry reaction, or in some variations, an EDC/sulfo-NHS reaction to prepare the modified sensor surface.

Figure 16:
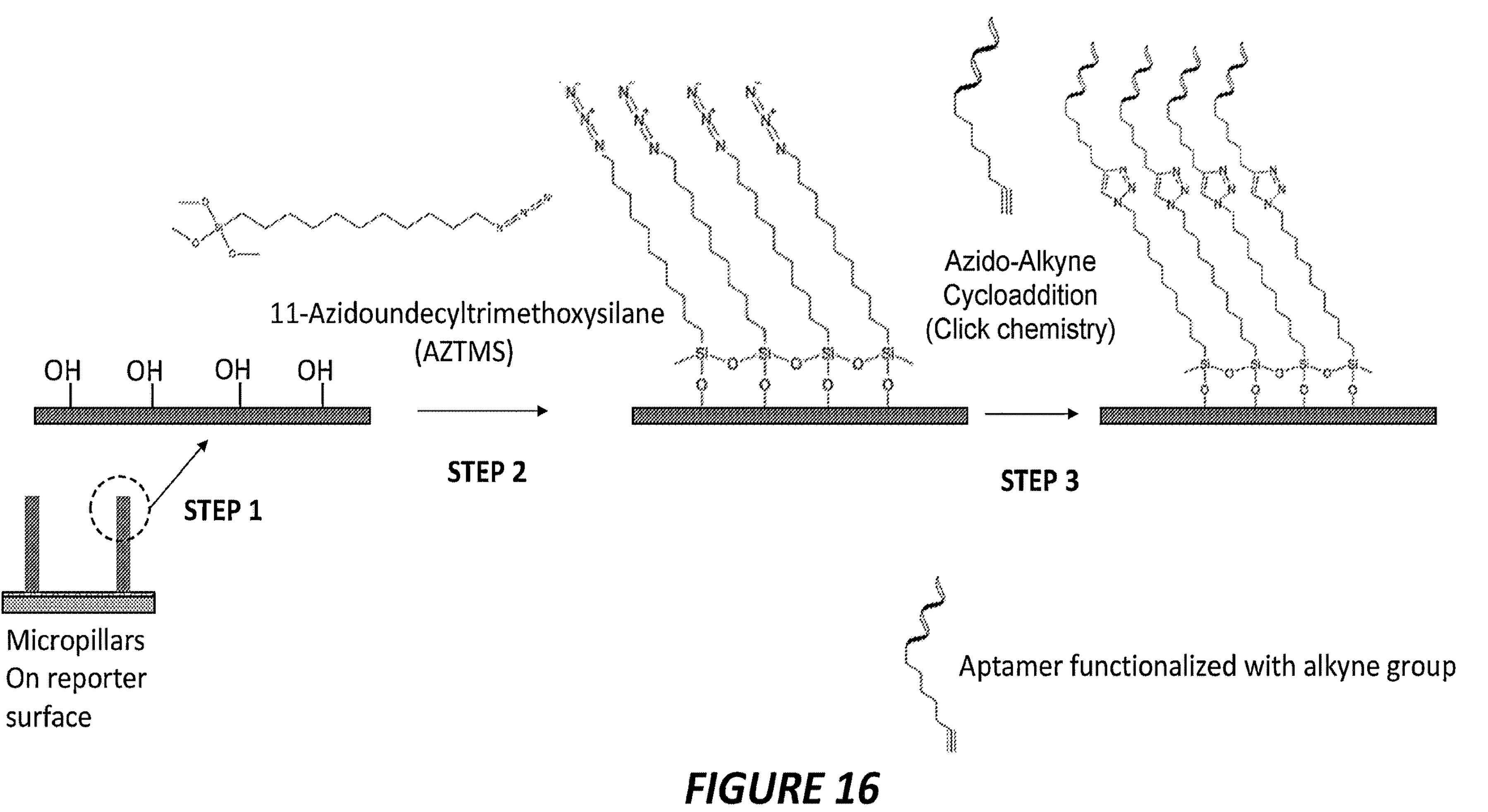
FIG. 16 shows a schematic of an exemplary method of conjugating an aptamer to a sensor surface via copper catalyzed azide alkyne cycloaddition (CuAAC) click chemistry, in accordance with some embodiments of the present invention.

FIG. 16 depicts another exemplary method for attaching aptamers to the sensor surface via click chemistry reaction in three steps. For example, STEP 1 may include an activation process to produce a hydroxyl-rich surface, as described above. STEP 2 includes a vapor phase reaction between an azide-bearing clickable silane molecule (e.g., 11-Azidoundecyltrimethoxysilane) with the hydroxyl groups on the sensor surface to form an azide rich surface. STEP 3 includes a copper catalyzed azide alkyne cycloaddition (CuAAC) click chemistry reaction between the azide-rich surface and an alkyne modified aptamers (see Rostovtsev, et al. Angew Chem Int Ed Engl, (2002) 41(14): 2596-2599; Moses, et al. Chem Soc Rev, (2007) 36(8): 1249-1262). The alkyne modified aptamers can be prepared using a standard oligo modification (e.g., from Integrated DNA Technologies). In some applications, other click chemistry attachments may be used including, but not limited to, strain promoted alkyne-azide cycloaddition (SPAAC), also referred to as the Cu-free click reaction, and the inverse electron demand Diels-Alder (IEDDA) click reaction (see Jewett, et al. (2010) Chem. Soc. Rev. 39(4): 1272; Ess, et al. (2008) Org. Lett. 10: 1633; Dommerholt, et al. Top. Curr. Chem. 374: 16). For example, in a SPAAC reaction, the azide modified aptamers, prepared by standard oligo modification, may be immobilized to the sensor surface via the reaction between the azide group and a dibenzocyclooctyne (DBCO) functionalized sensor surface. The DBCO surface may be produced from the reaction between a DBCO-NHS ester with an amine-rich surface, as described above.

In some other applications, the binding material 130 may be a molecularly imprinted polymer (MIP). Several approaches exist for manufacturing a MIP layer (Poma, et al. Trends in Biotechnology (2010), 28(12), 629-637; Haupt, et al, Chem. Rev. (2020), 120(17), 9554-9582; Xu et al, Methods in Enzymology, (2017), 590, 115-141. Giovannoli, et al., J. Mol. Recognit. (2012), 25: 377-382; Zimmerman, et al., Nature, (2002), 418, 399-403; Southard, et al., Macromolecules, (2007), 40(5) 1395-1400). In some embodiments, the MIP material for a MIP coating or a MIP layer may be manufactured by polymerization, e.g., by thermal and/or photochemical initiation of a mixture of monomers, cross-linkers, initiators, and/or porogens, or combinations thereof and the like. The MIP coating may be either grown in situ using either a "grafting-from" or a "grafting-to" approach. In a "grafting-from" approach, polymerization occurs at the sensor surface leading to the formation of a thin film of MIP coating to the sensor surface (e.g., see, Giovannoli, et al., J. Mol. Recognit. (2012), 25: 377-382). In a "grafting-to" approach, a MIP microparticle or nanoparticle or a soluble and processible MIP is produced initially from a thermal and/or photochemical polymerization (e.g., an emulsion polymerization) and then is attached (e.g., via a covalent bond) to the sensor surface (e.g., see, Xu et al, Methods in Enzymology, (2017), 590, 115-141). The choice of components (e.g., monomers, cross-linkers, initiators, and/or porogens, or combinations thereof and the like) for the polymerization mixture depends on the type and end use of the MIP material. Typical monomers include, for the purpose of illustration and not limitation, carboxylic acids (e.g., acrylic acid, methacrylic acid, vinylbenzoic acid, and trifluoromethyl acrylic acid (TFMAA)), sulphonic acids (e.g., 2-acrylamido-2-methylpropane sulphonic acid), heteroaromatic bases (e.g., vinylpyridine and vinylimidazole), acrylamide, 2-hydroxyethylmethacrylate (HEMA), and the like. Typical cross-linkers include, for the purpose of illustration and not limitation, ethylene glycol dimethacrylate (EGDMA), trimethylolpropane trimethacrylate (TRIM), divinylbenzene (DVB), pentaerythritol triacrylate (PETRA), and the like. Typical initiators include, for the purpose of illustration and not limitation, acetyl peroxide, lauroyl peroxide, decanoyl peroxide, caprylyl peroxide, benzoyl peroxide, tertiary butyl peroxypivalate, sodium percarbonate, tertiary butyl peroctoate, azobis-isobutyronitrile (AIBN), and the like. Typical porogens include, for the purpose of illustration and not limitation, methanol, acetonitrile, toluene, mineral oil, and combinations thereof. The polymerization may also be an emulsion polymerization to produce particle like MIPs (e.g. nanoparticles). Furthermore, the MIP particles may be covalently bound to the sensor surface via different conjugation approaches including but not limited to carbodiimide crosslinking chemistry, click chemistry, glutaraldehyde crosslinking chemistry, fluorous affinity, etc.

Figure 17:
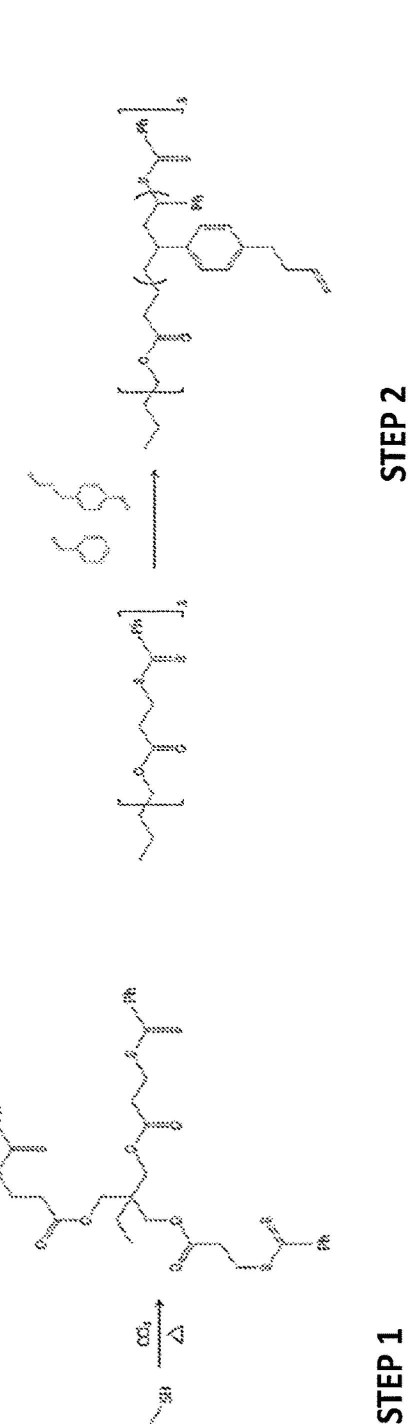
FIG. 17 shows a schematic of an exemplary method for producing a molecularly imprinted polymer for the target analyte ketamine, in accordance with some embodiments of the present invention.
Figure 17:
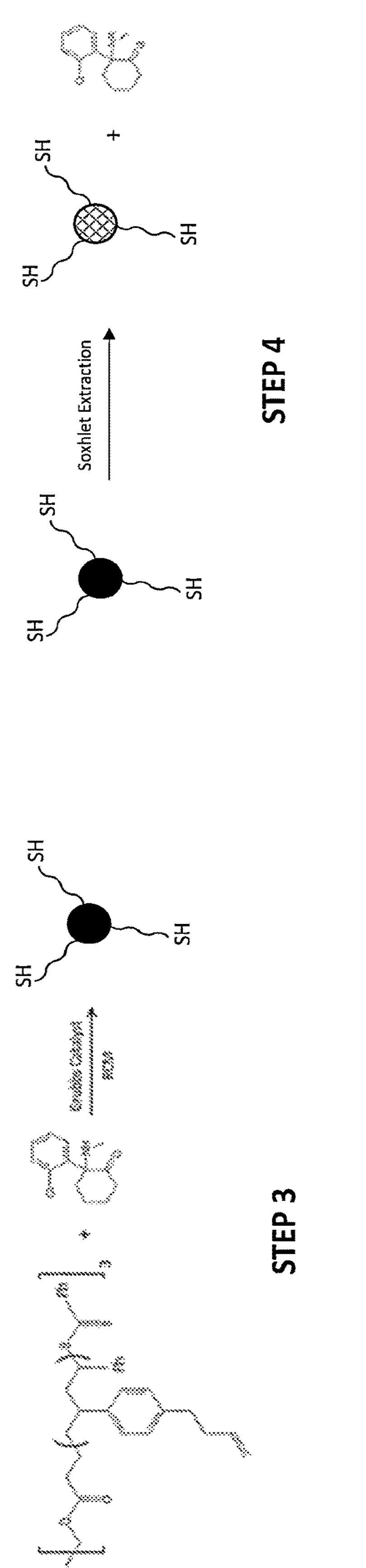

In some embodiments, a MIP layer or coating may be applied as a coating to the surficial walls defining all or a select number of the air gaps/voids. In various embodiments, a soluble and processible MIP layer is developed in a four-step process as shown in FIG. 17. In general, the soluble and processible MIP layer is made from a polymer with cross-linkable arms, e.g., a star-shaped polymer with cross-linkable arms, or a dendrimer with cross-linkable arms. The cross-linkable arms may contain one or more vinyl groups or other suitable functional groups that may be initiated and/or participate in a polymerization reaction. In FIG. 17, ketamine is used as an example target analyte for the molecularly imprinting process to produce the MIP, but other target analytes may also be used. In greater detail, STEP 1 may include a process or reaction to produce a star-shaped macroinitiator for controlled free radical polymerization. Then in STEP 2, a crosslinkable three-armed star polymer may be synthesized using controlled free radical polymerization methods such as RAFT (reversible-addition fragmentation chain-transfer) or ATRP (atom transfer radical polymerization), or by grafting end-functionalized polymer chains onto a multifunctional central core. The polymerization may incorporate a functional monomer into the chain that can be used to form crosslinks (e.g., 4-butenylstyrene, 2-(allyloxy)ethyl acrylate, and N-(hex-5-enyl)acrylamide). Subsequently in STEP 3, an imprinting process is performed by crosslinking the star polymer in the presence of the target analytes of interest (e.g., ketamine), which may form selective receptor binding sites around the target analytes. Crosslinking may be accomplished catalytically (e.g., cross-metathesis or ring closing metathesis (RCM) of olefin-terminated side chains catalyzed by Grubbs catalyst). The terminal functional groups (for example, thiol groups produced from RAFT polymerization) may allow the MIP polymers or coating or layer to be bound to the colorimetric sensor surface. As non-limiting examples, thiol groups facilitate bonding to metal surfaces, and polymers functionalized with a silanizing reagent may bond to glass. In a final STEP 4, a Soxhlet extraction process may be performed to extract the imprinted target analyte (e.g., ketamine) to yield a soluble and processible MIP. The MIP layer may be attached to the sensor surfaces using, for example, covalent bonds, non-covalent forces, ionic bonds, van der Waals forces, electrostatic forces, hydrogen bonding, fluorous affinity, Pi-Pi stacking interactions, and the like.

Figure 18:
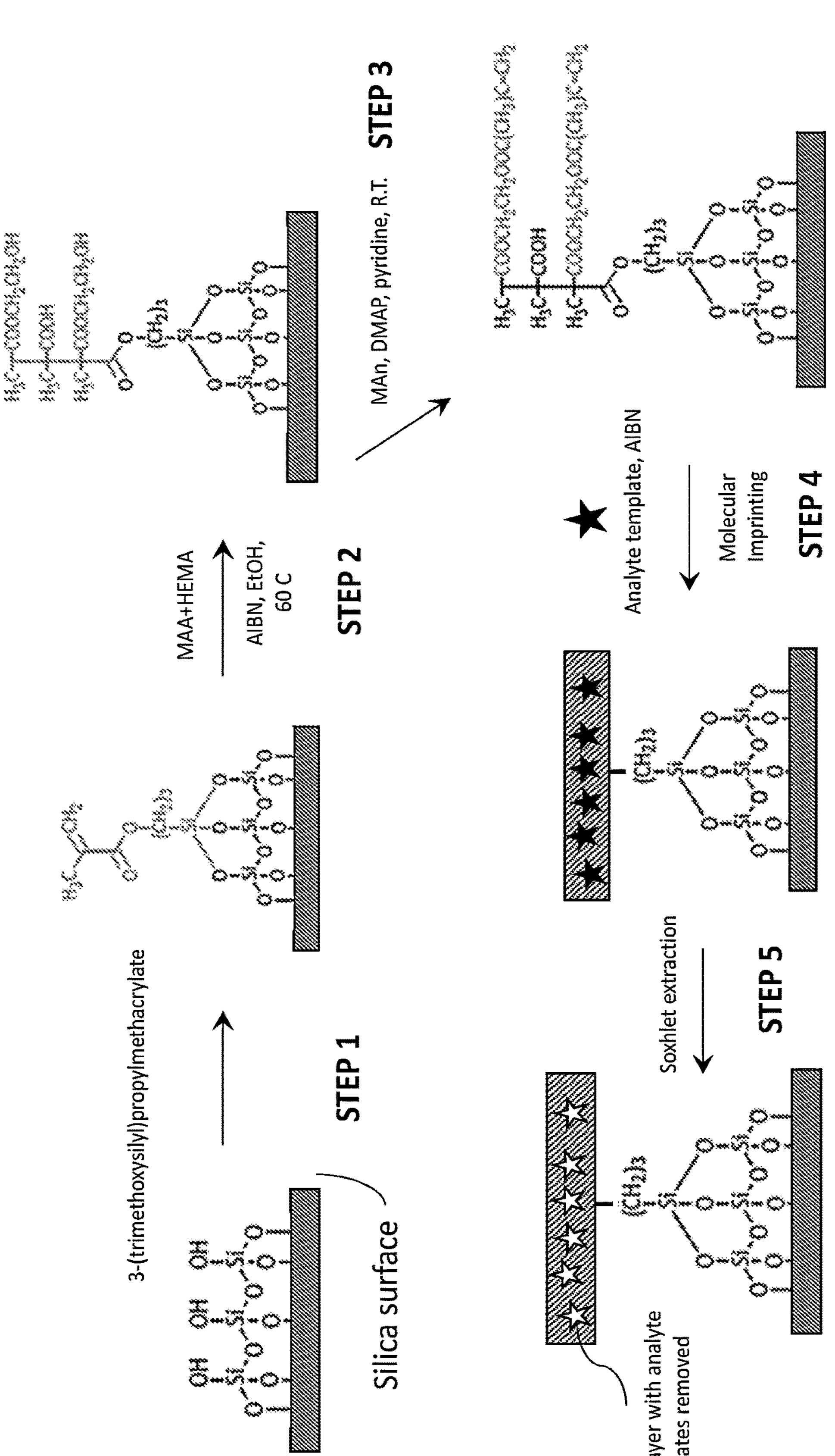
FIG. 18 shows a schematic of an exemplary method for grafting in situ a molecularly imprinted polymer layer for a target analyte of interest onto a sensor surface, in accordance with some embodiments of the present invention.

In some embodiments, the MIP layer may be produced, grown, or grafted in situ on the surficial walls of the transducer or the surficial walls defining all or a select number of the air gaps/voids. An exemplary five-step grafting process is illustrated in FIG. 18. As a non-limiting example, a silanization process is employed to functionalize the silica surface, e.g., of a pillar based transducer, with vinyl groups, from which a macromonomer can be grown via a "grafted" approach (as shown in the top row of FIG. 18 to the structure in the bottom row, right hand side). Target analyte molecules (e.g., ketamine, tetrahydrocannabinol, etc.) can be subsequently imprinted in situ in a MIP thin layer, e.g., using the soluble and processible MIP approach described herein, where the MIP thin layer may be on and/or attached to the surface of the silica of the pillar based transducer. Subsequently, the target analyte molecules may be removed using Soxhlet extraction method to form the MIP thin layer (as shown in the structure in the bottom row, left hand side of FIG. 18).

Figure 19:
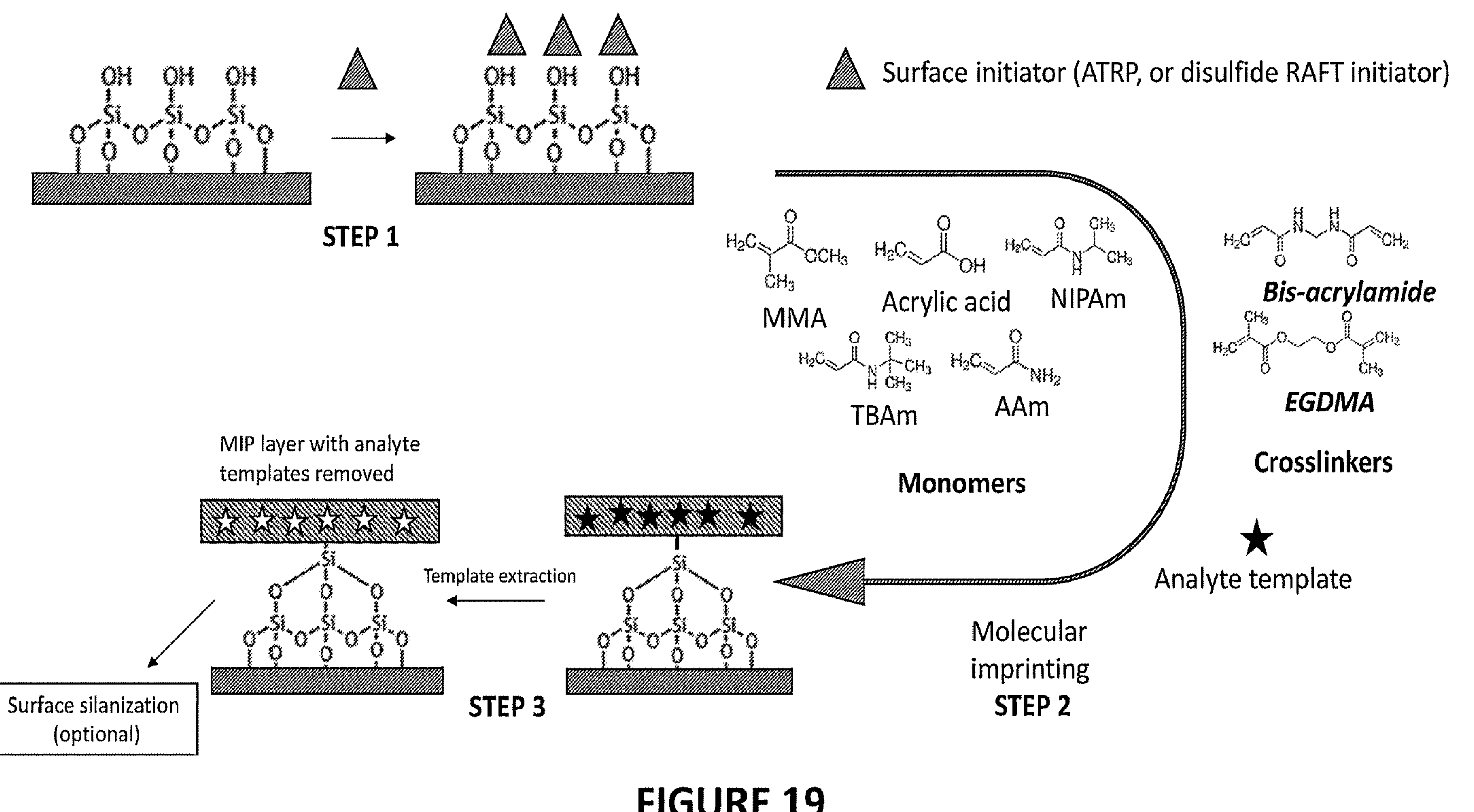
FIG. 19 shows a schematic of an exemplary method for grafting a molecularly imprinted polymer layer via a controlled polymerization process using a surface initiator, in accordance with some embodiments of the present invention.

In some other embodiments, the MIP layer may be produced, grown, or grafted in situ on the surficial walls of the transducer or the surficial walls defining all or a select number of the air gaps/voids via a controlled polymerization process. An exemplary three-step grafting process is illustrated in FIG. 19. As a non-limiting example, an initiator layer (e.g., a bromide based ATRP initiator, disulfide RAFT agent, etc.) may be grafted to the surficial wall surface in STEP 1 by reacting the initiator with an activated hydroxyl-rich surface. Then in STEP 2, a mixture of monomers (e.g., MMA, acrylic acid, NIPAm, TBAm, AAm, or the like) and crosslinkers (bis-acrylamide, EGDMA, and the like) can be polymerized into a MIP layer while the target analyte can be imprinted in situ in the MIP thin layer. The hydrophobicity/hydrophilicity of the resulting MIP can be tuned by selecting suitable hydrophobic or hydrophilic monomers. Subsequently in STEP 3, the analyte template may be removed by using extraction techniques (e.g., Soxhlet extraction, solvent extraction) to form receptor binding sites. An optional silanization step may be performed to produce a hydrophobic coating on the surface.

Alternative Wetting Mode-Based Sensing

The embodiments of the sensors described above transition from a "non-sticky" (or "slippery") Wenzel wetting mode to a "sticky" Wenzel wetting mode when an analyte of interest is present in a fluid. However, other wettability change formats may be employed as the readout signal for the indication of an analyte binding event. For the purpose of illustration rather than limitation, these additional wettability change formats may include a wettability change from a liquid-penetrated state (i.e., a state in which a fluid (e.g., a liquid) may penetrate an air gap/void or a plurality of air gaps/voids in the sensor) to a liquid repellent state (i.e., a state in which a fluid (e.g., a liquid) cannot penetrate an air gap/void or a plurality of air gaps/voids in the sensor), a wettability change from a hydrophilic state to a hydrophobic state, a wettability change from a "sticky" Wenzel mode to a "non-sticky" Wenzel mode, and/or a wettability change from a "sticky" Wenzel mode to a "non-sticky" Cassie mode.

Figure 20:
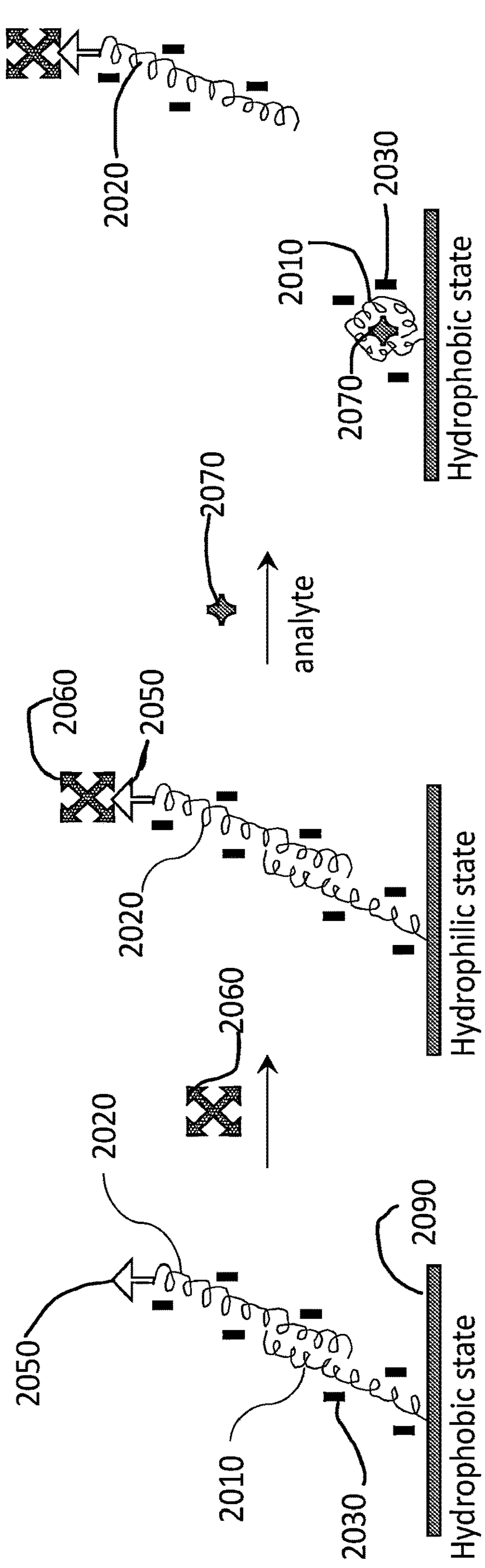
FIG. 20 shows a sensor undergoing a wettability change resulting from a transition from a hydrophilic state to a hydrophobic state, in accordance with some embodiments of the present invention.
Figure 20:
Figure 21:
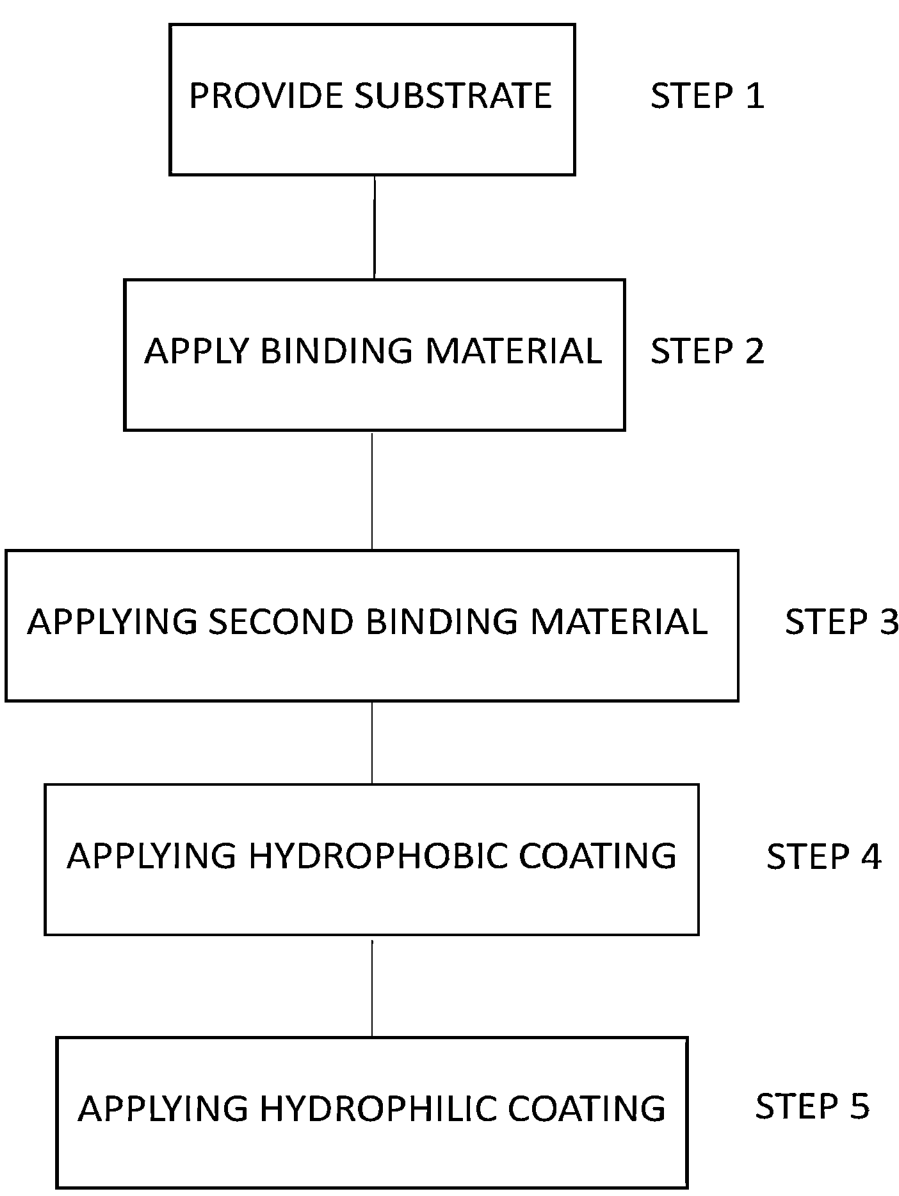
FIG. 21 shows a flow chart for manufacturing a wetting-based colorimetric sensor, such as the sensor shown in FIG. 20, in accordance with some embodiments of the present invention.

Referring to FIGS. 20 and 21, an exemplary method for designing a sensor with a surface chemistry that uses a wettability change from a hydrophilic state to a hydrophobic state using a competitive binding format is shown. In a first step, a substrate 2090—such as a substrate configured with a flat surface or a structured surface with transducers (e.g., as shown in FIG. 1)—may be provided (STEP 1). A target binding material 2010 (e.g., a capture aptamer) may be immobilized to the surface (STEP 2) of the substrate 2090, for example, using any of the attachment methods described above. Subsequently, a second auxiliary binding material 2020 (e.g., an oligonucleotide with a complementary sequence or partly complementary sequence) may be applied (STEP 3) to the surface of the substrate 2090 or, more particularly, the second auxiliary binding material 2020 may be applied to bind (e.g., weakly) to the target binding material 2010. A hydrophobic coating 2030 (e.g., a fluorinated silane, fluoropolymer, and the like) may be applied to the surface (STEP 4) of the substrate 2090 and/or to the target binding material 2010 (e.g., a capture aptamer) and/or to the auxiliary binding material 2020. In this condition, the sensor is in a hydrophobic state. Subsequently, hydrophilic components may be applied (e.g., bound to the second auxiliary binding material 2020) to enable a hydrophilic state (STEP 5). For example, as shown in FIG. 20, a biotin-modified aptamer 2050 may be used to bind avidin 2060 or streptavidin to the surface of the substrate 2090 to make it hydrophilic.

When a fluid that does not contain the target analyte of interest contacts the substrate 2090, the second auxiliary binding material 2020 remains bound to the surface and/or to the target binding material 2010. As a result, the substrate 2090 maintains a hydrophilic surface chemistry. As a result, although fluid may be able to infiltrate the air gaps/voids, the fluid cannot roll off the surface of the substrate 2090 when tilted or flipped. Thus, a "sticky" Wenzel wetting mode or the like may be observed.

However, when a fluid that does contain a target analyte of interest 2070 contacts the surface of the substrate 2090, the second auxiliary binding material 2020 that is only weakly bound to the surface of the substrate 2090 may be released from the surface due to competitive binding of the target analyte 2070 to the target binding material 2010. Releasing the second auxiliary binding material 2020 and its hydrophilic components produces a hydrophobic surface chemistry due to the hydrophobic coating 2030 disposed on the target binding material 2010 and, resultingly, fluid does not stick to the surface of the substrate 2090. As a result, the surface becomes "non-sticky" and fluid can roll off the surface of the substrate when the substrate 2090 is tilted or flipped. Thus, a "non-sticky" Cassie mode or the like may be observed.

In some other variations, fluid containing the target analyte of interest may penetrate the air gaps/voids of the transducer but be "non-sticky" to the surface, rolling off the surface when the substrate 2090 is tilted or flipped. Thus, a "non-sticky" Wenzel mode or the like may be observed.

In some alternative applications, when a fluid that does not contain the target analyte of interest contacts the surface of a sensor, an external trigger (e.g., an electrical voltage, a mechanical pressure, or the like) may be applied to the sensor to enable reversible penetration of the fluid into the air gaps/voids. Fluid will be prevented from penetrating into the air gaps/voids once the external trigger (e.g., an electrical voltage, a mechanical force, or the like) is removed; hence, a "non-sticky" Wenzel mode may be observed. When a fluid that does contain the target analyte of interest contacts the surface of the sensor, an external trigger (e.g., an electrical voltage, a mechanical pressure, or the like) may be applied to the sensor to enable reversible penetration of the fluid into the air gaps/voids. Target analyte binding to the surface changes the wettability so that fluid remains trapped in the air gaps/voids after the external trigger (e.g., an electrical voltage, a mechanical force, or the like) is removed; hence a "sticky" Wenzel wetting mode or the like may be observed.

Non-Specific Binding

To specifically detect a target analyte in a complex matrix that includes target and non-target analytes or objects using a wetting mode-based sensor, the non-specific binding of non-target analytes or objects needs to be suppressed. With a "non-sticky" Wenzel mode sensor, the hierarchical structure, including nanoscale features, may be coated with a hydrophobic layer to produce a nanotribological system to reduce the friction or adhesion of non-target analytes or objects in a fluidic flow. For example, a wash step (e.g., using a surfactant, salt solution, or combination thereof) may be used to remove the non-specific bound non-target analytes or objects (e.g. molecules, proteins, nucleic acids, and the like) so that only the target analytes remain bound to the sensor surface and, thereby, induce a "sticky" Wenzel mode.

Figures 22A, 22B, 22C:
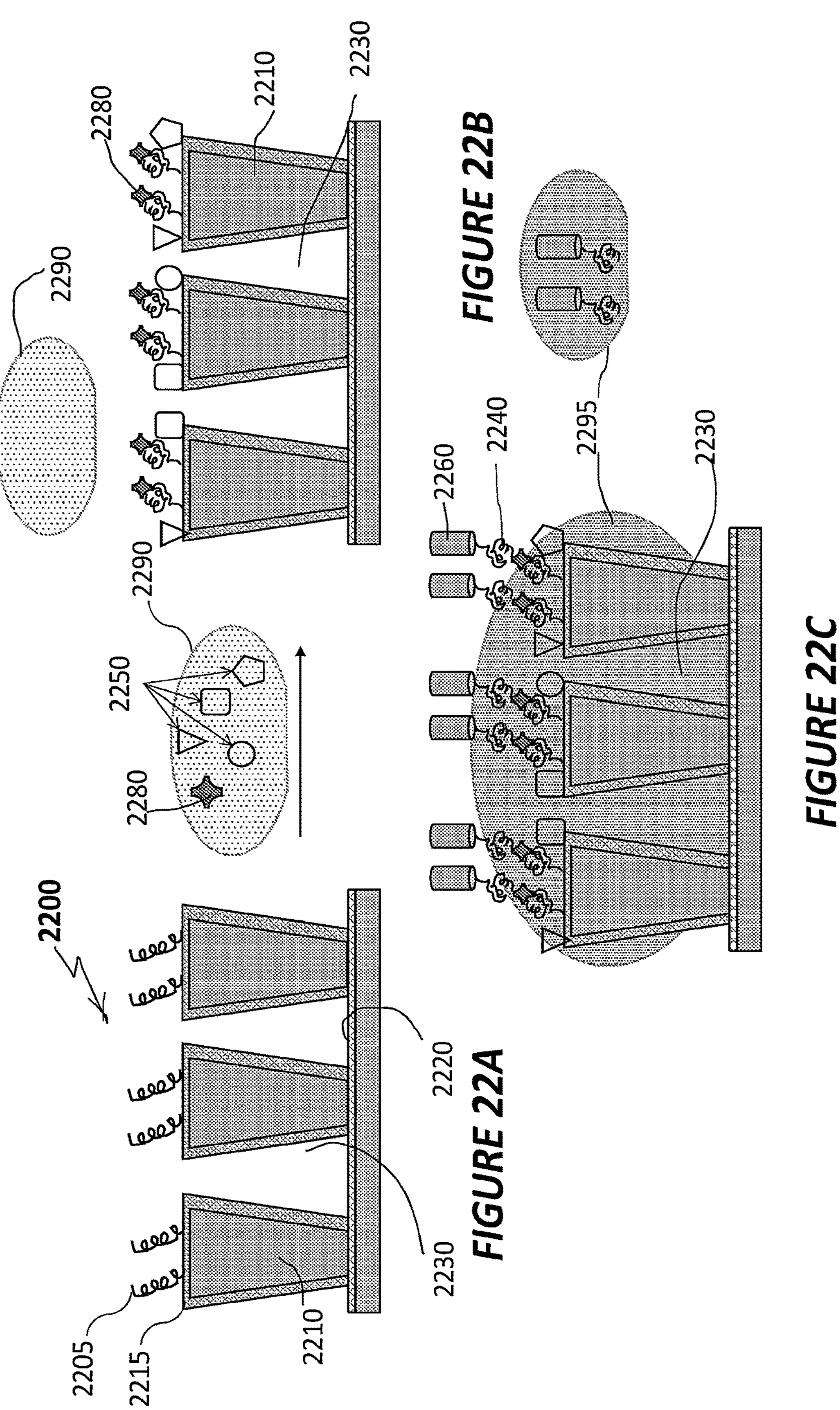
FIGS. 22A-22C show an inverted-frustoconical-shaped reentrant structure sensor with an aptamer binding material for suppressing non-specific binding from a complex matrix, in accordance with some embodiments of the present invention.

To reduce non-specific binding, a blocking treatment step of the sensor may also be used. For the purpose of illustration rather than limitation, blocking buffers may include protein blocking agents such as Bovine Serum Albumin (BSA) or non-protein blocking agents such as polyvinylpyrrolidone (PVP). As shown in FIGS. 22A-22C, in some embodiments, a colorimetric sensor 2200 may include a plurality of reentrant structures 2210 (e.g., having an inverted frustoconical-shaped structure) operatively disposed on an indicator 2220. Although FIGS. 22A-22C show an embodiment of a sensor 2200 having three inverted frustoconical-shaped reentrant structures 2210 disposed on the indicator 2220, this is done for the purpose of illustration rather than limitation. Indeed, any number of reentrant structures 2210, any shape of reentrant structures 2210, and any arrangement or distribution of reentrant structures 2210 on the surface of the indicator 2220 may be used. For example, the reentrant structures 2210 may be formed in a periodic, aperiodic, and/or random array. The reentrant structures 2210 may be micro- or nano-hoodoo structures, T-shaped structures, doubly reentrant structures, or the like.

Advantageously, in some implementations, the colorimetric sensor 2200 may be used in two steps. In the first step, a fluid 2290 (e.g., a saliva or blood sample) that contains a complex matrix that includes target 2280 and non-target 2250 analytes or objects is allowed to penetrate into the air gaps/voids 2230 between adjacent inverted frustoconical structures 2210. The fluid (e.g., liquid) 2290 is still allowed to exit the air gaps/voids 2230 when the sensor 2200 is flipped or tilted. After the initial matrix binding (which may include the specific binding of target analyte 2280 to aptamer 2205, the non-specific binding of target analyte 2280 to aptamer 2205, the non-specific binding of target analyte 2280 to the hydrophobic surface coating material 2215, the non-specific binding of non-target analyte 2250 to aptamer 2205, and the non-specific binding of non-target analyte 2250 to the hydrophobic surface coating material 2215), the surface of the sensor 2200 may still be hydrophobic enough to enable a "non-sticky" Wenzel mode. However, the surface hydrophobicity of the sensor 2200 may have been reduced to a level at which a small additional increase of hydrophilicity induces a wetting state transition, for example, from a "non-sticky" Wenzel state to a "sticky" Wenzel state. Subsequently, in a second step, a secondary fluid 2295 that contains only a binding molecule may be introduced to the sensor 2200 to allow its binding to the bound target 2280, which in turn increases the hydrophilicity of the surface and enables a transition from a "non-sticky" Wenzel mode to a "sticky" Wenzel mode. The sensor device 2200 may then be tilted or flipped to read out the signal.

As a non-limiting example, the secondary binding molecule may use another aptamer or antibody 2240 as the probe to induce the wetting transition from "non-sticky" Wenzel mode to "sticky" Wenzel mode. More particularly, the secondary probe aptamer 2240 may be a hydrophilic aptamer itself and/or may be further tagged with a hydrophilic element 2260 to increase the hydrophilicity (e.g., to the 5' or 3' end of the secondary probe aptamer 2240). As a result, after the introduction of the secondary probe aptamer 2240, the liquid 2295 may become trapped between the inverted frustoconical structures 2210. Once trapped, the fluid 2295 cannot roll off the surface of the sensing device 2200 when the sensing device 2220 is tilted or flipped.

In some other embodiments, additional polymer layers may be applied to the surface of the transducer. In a non-limiting example, polymer brushes may be grown on the surficial walls or part of the surficial walls of the transducer to reduce the non-specific binding of non-target analytes or objects. Polymer brushes are well known to effectively resist the non-specific binding, due to the strong suppression of ionic attraction between the solid substrate and the non-target analytes or objects. For example, a zwitterion polymer brush that has the same number of anionic and cationic groups may be used to repel unwanted adhesions of non-target analytes or objects with a hydration layer formed from the ionic solvation effect. As a non-limiting example, the polymer brush may be an oligo (ethylene glycol), poly(oligo(ethylene glycol) methyl ether methacrylate (POEGMA), poly(2-methacryloyloxyethyl phosphorylcholine), and the like. The polymer brushes may be grafted to the surficial walls or some portion of the surficial walls of the transducer via surface-initiated controlled free radical polymerization techniques. For the purpose of illustration rather than limitation, exemplary surface-initiated controlled free radical polymerization techniques include RAFT (reversible-addition fragmentation chain-transfer), ATRP (atom transfer radical polymerization), and the like.

In some variations, the polymer brushes may be used as an anchor to immobilize the binding materials (e.g., aptamers, antibodies, MIPs, combinations thereof, and the like). Indeed, in some other variations, the polymer brushes may be formed from hydrophobic monomers or formed from hydrophilic monomers that are coated with hydrophobic molecules. For the purpose of illustration rather than limitation, exemplary hydrophobic molecules include compounds with long alkyl chains, fluorinated silanes (e.g., 1H,1H,2H,2H-perfluorooctyltrichlorosilane, octadecyltrichlorosilane, and the like), organofluorine compounds, perfluorocarbons, fluoropolymers, hydrofluorocarbons, fluorocarbenes, and combinations thereof.

Figure 23:
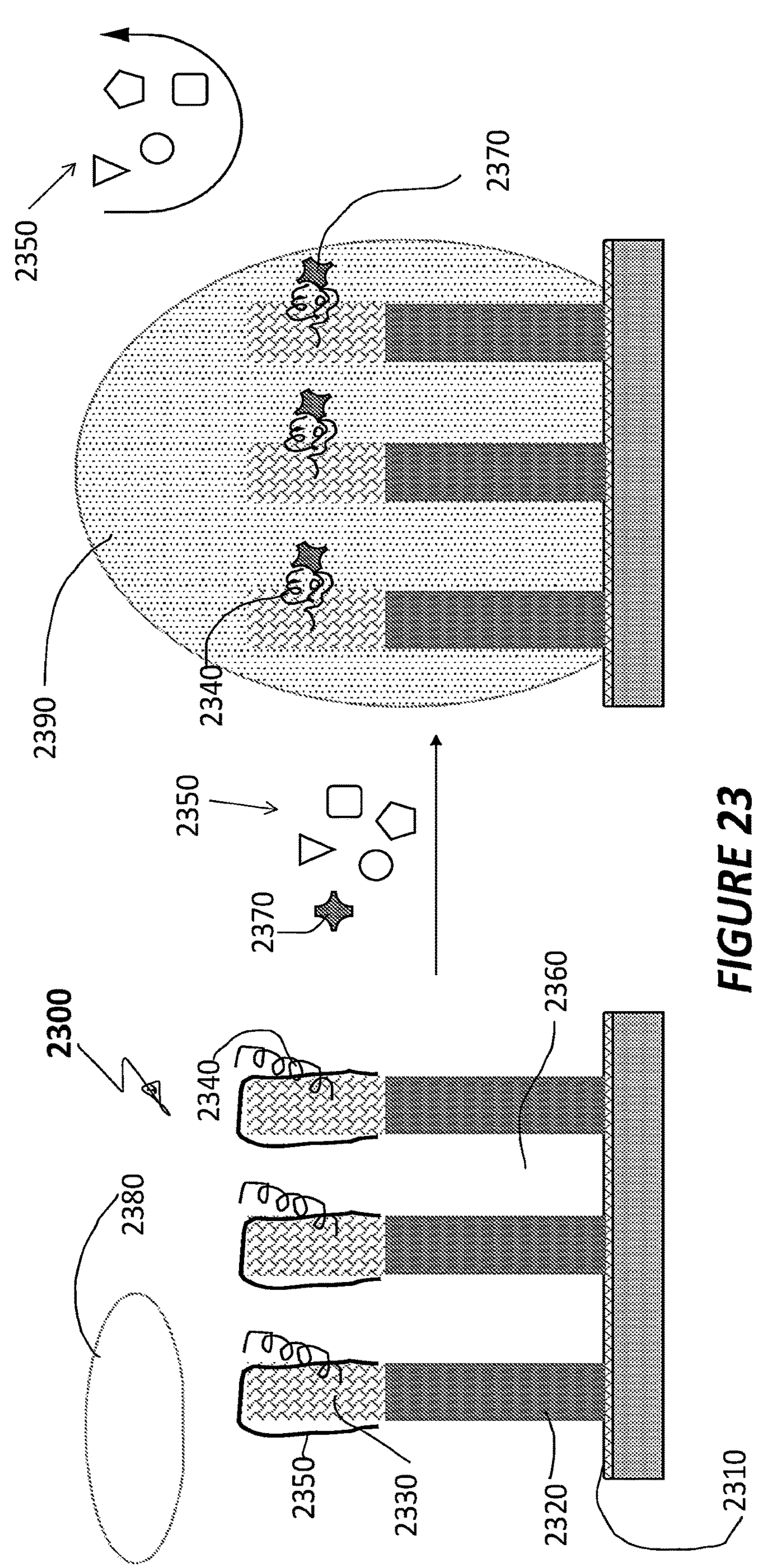
FIG. 23 shows a sensor having polymer brushes with a hydrophobic coating for suppressing non-specific binding from a complex matrix, in accordance with some embodiments of the present invention.

For example, referring to FIG. 23, a colorimetric sensor 2300 having a plurality of polymer brushes 2330 grown on the surfaces of microstructures and/or nanostructures 2320 (e.g., micropillars and/or nanopillars) along with a binding material 2340 (e.g. aptamers) and hydrophobic coating 2350 (e.g. a fluorinated silane, fluoropolymer, or the like) is shown. Although FIG. 23 shows a cross-section of an embodiment having three microstructures and/or nanostructures 2320, this is done for the purpose of illustration rather than limitation. Indeed, any number of microstructures and/or nanostructures 2320, any shape of microstructures and/or nanostructures 2320, and any arrangement or distribution of microstructures and/or nanostructures 2320 on the surface of the indicator 2310 may be used. In this type of sensor 2300, a transition from a "non-sticky" Wenzel mode (or the like) to a "sticky" Wenzel mode (or the like) may be used as the sensing mechanism.

For example, when a fluid 2380 that does not contain the target analyte of interest contacts the surfaces of the microstructures and/or nanostructures 2320, the fluid 2380 may be able to infiltrate the air gaps/voids 2360 disposed between adjacent microstructures and/or nanostructures 2320; however, because there is no target analyte of interest 2370 present in the fluid 2380 to bind to the binding material 2340, the fluid 2380 can roll off of the surface of the sensor 2300 when the sensor 2300 is tilted or flipped. In short, a "non-sticky" Wenzel wetting mode or the like may be observed.

Alternatively, if a fluid 2390 that contains the target analyte of interest 2370 contacts the surfaces of the microstructures and/or nanostructures 2320, the fluid 2390, which may also contain non-target analytes or objects 2350, may also infiltrate all or part of the air gaps/voids 2360 disposed between adjacent microstructures and/or nanostructures 2320. But, because there are target analytes of interest 2370 present in the fluid 2390 to bind to the binding material 2340, the fluid 2390 will be trapped in all or part of the air gaps/voids 2360 and, as a result, the fluid 2390 will not be able to roll off of the surface of the sensor 2300 when the sensor 2300 is tilted or flipped. In other words, a "sticky" Wenzel mode or the like may be observed. The presence of the fluid 2390 in the air gaps/voids 2360 modifies the refractive index of the sensor 2300, thus leading to an observable color change.

Figures 24A, 24B:
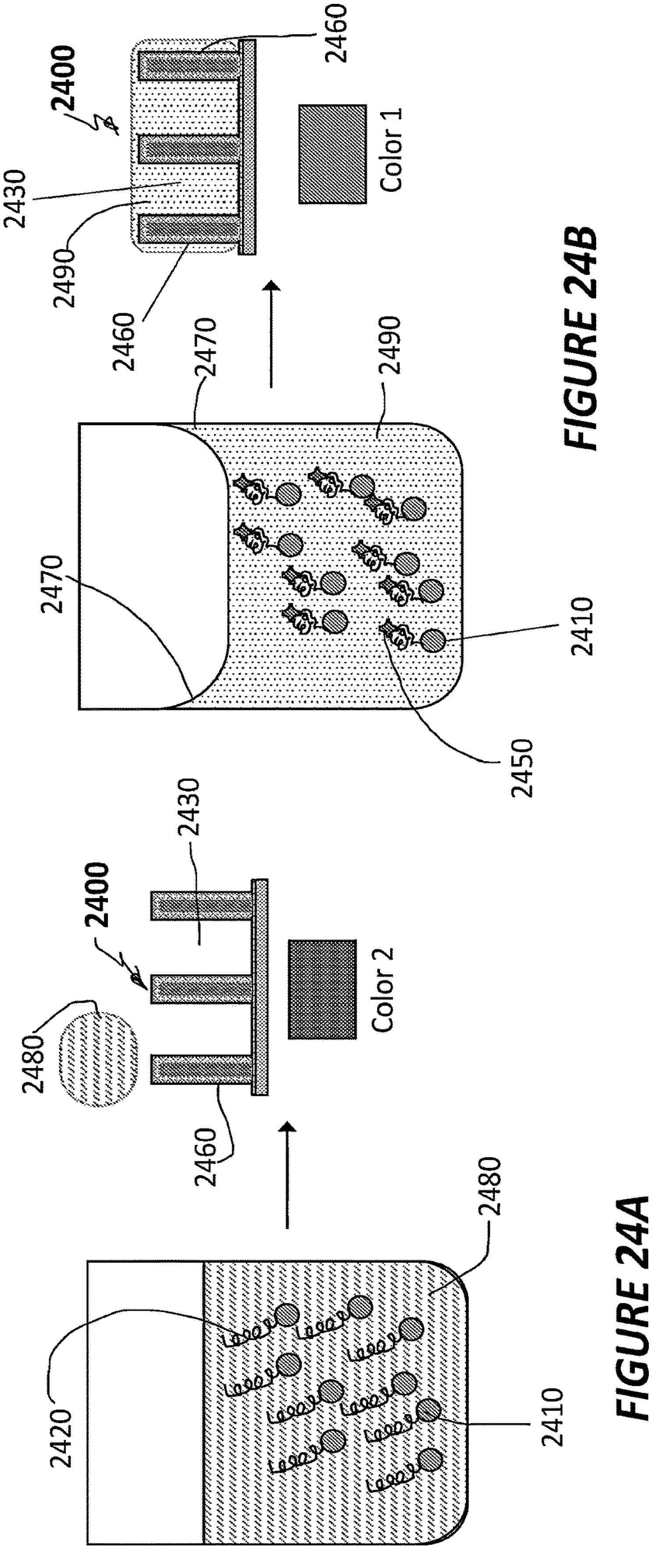
FIGS. 24A and 24B show sensors used in combination with a colloidal nanoparticle solution that, respectively, do not include a target analyte of interest and include a target analyte of interest, in accordance with some embodiments of the present invention.

In some applications of the invention, a colloidal nanoparticle solution may be used as an auxiliary part in combination with a colorimetric sensor. For example, as shown in FIG. 24A, (e.g., colloidal) nanoparticles 2410 (e.g., colloidal gold nanoparticles, magnetic nanoparticles, latex nanoparticles, silica nanoparticles, combinations thereof, and the like) may be conjugated with a binding material 2420 (e.g., aptamers, antibodies, MIPs) and dispersed in a fluid to form the auxiliary colloidal nanoparticle solution 2480. In some variations, the nanoparticles 2410 may be functionalized with polymer brushes or the like (e.g., polyethylene glycol) and may be pre-exposed with blocking buffers (e.g. protein or non-protein blocking agents) to reduce the non-specific binding from non-target objects.

As shown in FIG. 24A, when another fluid that does not contain the target analyte of interest is added into the colloidal solution 2480, the interfacial tension between the nanoparticles 2410 and the fluid 2480 remains unchanged.

The interfacial tension results from the interaction between two different phases (e.g., the solid phase of the colloidal particles and the liquid phase of the solvent) and affects the surface tension of the fluid (e.g., the colloidal solution) when interacting with a surface. Subsequently, when the mixed colloidal solution 2480 is introduced into a wetting-based colorimetric sensor 2400, the solution 2480 may be able to infiltrate the air gaps/voids 2430. However, because there is no target analyte of interest to bind with a binding material 2460, the fluid 2480 does not stick to (e.g., adhere to, attach to, be adsorbed by, and the like) the surficial walls of the sensor 2400 defining the air gaps/voids 2430. Hence, the fluid 2480 is able to exit the air gaps/voids 2430 and roll off of the surface of the sensor 2400 when the sensor 2400 is tilted or flipped. As a result, a color (e.g., "Color2") associated with a "non-sticky" Wenzel wetting mode and indicative of the absence of the analyte of interest in the fluid 2480 may be observed.

As shown in FIG. 24B, when a fluid 2490 that contains the target analyte of interest 2450 is added into the colloidal solution, a target binding event may induce a change in the interfacial tension between the nanoparticles 2410 and the fluid 2490, which results in a surface tension change of the colloidal solution. Subsequently, when adding the mixed colloidal solution 2490 onto the wetting-based sensor 2400, the fluid 2490 may be allowed to infiltrate all or part of the air gaps/voids 2430. Moreover, because target analytes of interest 2450 are present in the colloidal solution 2490, the target analyte of interest 2450 may bind with the binding material 2460; hence, the fluid 2490 sticks to (e.g., adheres to, attaches to, is adsorbed by, and the like) the sensor 2400. The surface tension change of the colloidal solution (e.g., a lower surface tension due to the interfacial tension change) also enhances the wetting and thus the stickiness of the fluid to the surface so that a higher color contrast may be achieved. As a result, a color (e.g., "Color1") associated with a "sticky" Wenzel mode and indicative of the presence of the analyte of interest 2450 in the fluid 2490 may be observed. More specifically, the presence of the fluid 2490 in the air gaps/voids 2430 modifies the refractive index of the sensor, thus leading to an observable color change (e.g., from "Color2" to "Color1").

In some implementations, the binding induced interfacial tension (or wettability) change may be directly visualized from the colloidal solution itself. As shown in FIG. 24B, when the inner surface of the container is hydrophobic, a change of the original flat liquid surface to a meniscus 2470 formed in such a container may be visible when another fluid that contains the target analyte of interest 2450 is added into the colloidal solution 2490.

In some other implementations, the auxiliary colloidal solution may be used as an amplification method to enhance the readout from the wetting-based sensor 2400. For a non-limiting example, the surface of the wetting-based sensor 2400 may be coated with a first aptamer 2460 for the target analyte of interest 2450. The colloidal nanoparticles 2410 may be functionalized with a second aptamer 2420 for the same target analyte of interest 2450. In the example, the second aptamer 2420 differs from the first aptamer 2460, notwithstanding that both aptamers 2420, 2460 are adapted to bind to the same target analyte of interest (e.g., in different binding regions of a protein analyte, in different epitopes of an antigen, and so forth). For example, the two aptamers 2420, 2460 may form a sandwich-like configuration to amplify the readout signal when a fluid that contains the target analyte of interest 2450 is added to the auxiliary colloidal solution and the wetting-based sensor 2400. Those of ordinary skill in the art can appreciate that, in some applications, more than two aptamers may be used to further amplify the readout signal.

EXAMPLE

In some embodiments, for example referring to FIGS. 25A and 25B, the sensors or sensor arrays 2500 described herein may appear to be a flat surface. Although the sensor 2500 surface may appear to be flat or planar, the sensor 2500 may in fact include nanometer-scaled features (including nano-scaled surface roughness) that cannot be directly visualized by the naked human eye without the aid of microscopy imaging tools (e.g., a scanning electron microscope) and such an apparently flat surface may be configured to function in the same way as a surface with visible microstructures. FIGS. 25A and 25B show optical photographs of sensor chips 2500 fabricated with nanometer-scale surface roughness and coated with (i) an aptamer material that specifically binds to beta-2-transferrin (b2TR) protein (a biomarker in cerebrospinal fluid) and (ii) a hydrophobic material. FIG. 25A shows the b2TR sensor surface is "non-sticky" after being contacted with a fluid that does not contain a target analyte of interest (e.g., a fluid that contains 10 μg/mL bovine serum albumin protein). As shown, the fluid is allowed to roll off of the surface of the sensor 2500. FIG. 25B shows that the b2TR sensor surface becomes "sticky" after being contacted with a fluid that does contain the target analyte of interest, namely a fluid that contains 10 μg/mL b2TR protein). Accordingly, as shown, the fluid cannot roll off of the surface of the sensor 2500.

INCORPORATION BY REFERENCE

The entire disclosures of each of the patent documents and scientific articles cited herein are incorporated by reference herein in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A sensor for detecting an analyte of interest in a fluid sample, the sensor comprising:

a structure comprising a plurality of surficial walls that define a plurality of air gaps in the structure, the structure configured such that both a fluid sample lacking the analyte of interest and a fluid sample comprising the analyte of interest will penetrate the plurality of air gaps; and a binding material, present on the plurality of surficial walls, configured to bind to the analyte of interest, wherein the sensor is configured such that, when the analyte of the interest of the fluid sample comprising the analyte of interest binds to the binding material, a change in surface energy results within the plurality of surficial walls, such that the change in the surface energy within the plurality of surficial walls is configured to prevent the fluid sample comprising the analyte of interest from exiting the plurality of air gaps, and when the fluid sample lacks the analyte of interest, a lack of the change in the surface energy within the plurality of surficial walls is configured to allow the fluid sample lacking the analyte of interest to exit the plurality of air gaps.

2. The sensor of claim 1 further comprising a plurality of first structural elements coupled to at least one surficial wall of the plurality of surficial walls, the at least one surficial wall comprising a first order dimension and the plurality of first structural elements comprising a second order dimension of lower order than the first order dimension.

3. The sensor of claim 2, wherein the first order dimension comprises a micrometer scale and the second order dimension comprises a nanometer scale.

4. The sensor of claim 2 further comprising a plurality of second structural elements coupled to at least one first structural element, the plurality of second structural elements comprising a third order dimension of lower order than the second order dimension.

5. The sensor of claim 4, wherein the first order dimension comprises a millimeter scale, the second order dimension comprises a micrometer scale, and the third order dimension comprises a nanometer scale.

6. The sensor of claim 1, wherein the plurality of surficial walls of the structure are roughened.

7. The sensor of claim 1, wherein the binding material is at least one of a molecularly-imprinted polymer (MIP) material, aptamer, slow off-rate modified aptamer (SOMAmer), affimer, antibody, peptide, nucleic acid, deoxyribonucleic acid (DNA), ribonucleic acid (RNA), peptide nucleic acid (PNA), oligonucleotide, coordination complex, metal organic framework (MOF) material, porous coordination polymer material, and combinations thereof.

8. The sensor of claim 1, wherein the binding material further comprises at least one of a specific binding enhancement layer or an additional layer to reduce non-specific binding from non-target substances contained in the fluid sample.

9. The sensor of claim 1 further comprising a plurality of polymer brushes coupled to the plurality of surficial walls.

10. The sensor of claim 1, wherein the binding material is at least one of: produced from hydrophobic components, produced from hydrophilic components that are coated with a hydrophobic layer, or combinations thereof.

11. The sensor of claim 1 further comprising a hydrophobic material coated on the plurality of surficial walls.

12. The sensor of claim 1 further comprising a colorimetric indicator.

13. A method for detecting an analyte of interest in a fluid sample, the method comprising:

(a) contacting a sensor with a fluid sample, the sensor comprising:

(i) a structure comprising a plurality of surficial walls that define a plurality of air gaps in the structure, the structure configured such that both a fluid sample lacking the analyte of interest and a fluid sample comprising the analyte of interest will penetrate the plurality of air gaps; and (ii) a binding material, present on the plurality of surficial walls, configured to bind to the analyte of interest, wherein the sensor is configured such that, when the fluid sample comprising the analyte of interest binds to the binding material, a change in surface energy results within the plurality of surficial walls, such that the change in the surface energy within the plurality of surficial walls prevents the fluid sample comprising the analyte of interest from exiting the plurality of air gaps, and when the fluid sample lacks the analyte of interest, a lack of the change in the surface energy within the plurality of surficial walls allows the fluid sample lacking the analyte of interest to exit the plurality of air gaps; and (b) determining whether the fluid sample comprises the analyte of interest by observing the sensor.

14. The method of claim 13, wherein step (b) comprises observing a color exhibited by the sensor.

15. The method of claim 13, wherein the sensor further comprises a plurality of first structural elements coupled to at least one surficial wall of the plurality of surficial walls, the at least one surficial wall comprising a first order dimension and the plurality of first structural elements comprising a second order dimension of lower order than the first order dimension.

16. The method of claim 13, wherein the binding material includes at least one of a molecularly-imprinted polymer (MIP) material, aptamer, slow off-rate modified aptamer (SOMAmer), affimer, antibody, protein, peptide, nucleic acid, deoxyribonucleic acid (DNA), ribonucleic acid (RNA), peptide nucleic acid (PNA), oligonucleotide, coordination complex, metal organic framework (MOF) material, porous coordination polymer materials, and combinations thereof.

17. The method of claim 13, wherein the binding material further comprises at least one of a specific binding enhancement layer or an additional layer to reduce non-specific binding from non-target substances contained in the fluid sample.

18. The method of claim 13, wherein the sensor further comprises a colorimetric indicator.

19. A method comprising:

manufacturing a sensor, the sensor comprising:

a structure comprising a plurality of surficial walls that define a plurality of air gaps in the structure, the structure configured such that both a fluid sample lacking an analyte of interest and a fluid sample comprising the analyte of interest will penetrate the plurality of air gaps; and a binding material, present on the plurality of surficial walls, configured to bind to the analyte of interest, wherein the sensor is configured such that, when the analyte of interest in the fluid sample comprising the analyte of interest binds to the binding material, a change in surface energy results within the plurality of surficial walls, such that the change in the surface energy within the plurality of surficial walls prevents the fluid sample comprising the analyte of interest from exiting the plurality of air gaps, and when the fluid sample lacks the analyte of interest, a lack of the change in the surface energy within the plurality of surficial walls allows the fluid sample lacking the analyte of interest to exit the plurality of air gaps.

* * * * *